(12) United States Patent
Møller et al.

(10) Patent No.: US 8,361,036 B2
(45) Date of Patent: Jan. 29, 2013

(54) INJECTION DEVICE HAVING A GEARING ARRANGEMENT

(75) Inventors: Claus Schmidt Møller, Fredensborg (DK); Bennie Peder Smiszek Pedersen, Haslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 875 days.

(21) Appl. No.: 12/282,446

(22) PCT Filed: Mar. 8, 2007

(86) PCT No.: PCT/EP2007/052177
§ 371 (c)(1),
(2), (4) Date: Oct. 28, 2008

(87) PCT Pub. No.: WO2007/104697
PCT Pub. Date: Sep. 20, 2007

(65) Prior Publication Data
US 2009/0062748 A1 Mar. 5, 2009

Related U.S. Application Data

(60) Provisional application No. 60/784,775, filed on Mar. 22, 2006.

(30) Foreign Application Priority Data

Mar. 10, 2006 (EP) .................................... 06004932

(51) Int. Cl.
*A61M 5/00* (2006.01)
(52) U.S. Cl. ...................................................... 604/211
(58) Field of Classification Search .......... 604/207–211, 604/181, 187, 218
See application file for complete search history.

(56) References Cited

U.S. PATENT DOCUMENTS
(Continued)

FOREIGN PATENT DOCUMENTS
AU 2003232576 1/2004
CA 2359375 7/2000
(Continued)

OTHER PUBLICATIONS

Abandonment mailed on Oct. 8, 2009 in U.S. Appl. No. 11/911,869, filed on Oct. 18, 2007 by Glejbol et al.
(Continued)

*Primary Examiner* — Kevin C Sirmons
*Assistant Examiner* — Imani Hayman
(74) *Attorney, Agent, or Firm* — Wesley A. Nicolas; Marc A. Began; Reza Green

(57) ABSTRACT

An injection device with a gearing arrangement providing a gearing ratio between axial movement of an injection button and axial movement of a piston rod. The injection device comprises a dose setting member being operable to set a dose by rotating the dose setting member relatively to a housing, about a rotational axis. During setting of a dose the gearing arrangement is prevented from rotating along with the dose setting member about the rotational axis. Thereby the space which it is necessary to accommodate to the gearing arrangement inside the housing is reduced. This provides the possibility of using this space for other purposes, such as additional electronic components, designing the injection device in a manner which is appropriate for other purposes, e.g. with a relatively flat cross section, or reducing the overall size of the injection device. According to one aspect of the invention, the gearing arrangement comprises at least one gear wheel having a rotational axis which is non-parallel to, e.g. substantially perpendicular to, the rotational axis of the dose setting member. According to another aspect of the invention, the gearing arrangement comprises a driving spindle being provided with a threaded portion having a first pitch, and the piston rod is provided with a threaded portion having a second pitch. The gearing is provided by the threaded portions.

8 Claims, 15 Drawing Sheets

U.S. PATENT DOCUMENTS

| | | |
|---|---|---|
| 854,399 A | 5/1907 | Bridge |
| 2,392,196 A | 1/1946 | Smith |
| 2,956,563 A | 10/1960 | Sarnoff |
| 3,110,310 A | 11/1963 | Cislak |
| 3,115,135 A | 12/1963 | Sarnoff |
| 3,144,178 A | 8/1964 | Sarnoff et al. |
| 3,556,099 A | 1/1971 | Knight et al. |
| 3,880,162 A | 4/1975 | Simmons |
| 3,944,843 A | 3/1976 | Vaz Martins |
| 4,026,288 A | 5/1977 | Costa et al. |
| 4,231,368 A | 11/1980 | Becker |
| 4,275,727 A | 6/1981 | Keeri-Szanto |
| 4,277,227 A | 7/1981 | Jenkins |
| 4,298,000 A | 11/1981 | Thill et al. |
| 4,300,554 A | 11/1981 | Hessberg et al. |
| 4,313,439 A | 2/1982 | Babb et al. |
| 4,314,556 A | 2/1982 | Ma |
| 4,368,731 A | 1/1983 | Schramm |
| RE31,315 E | 7/1983 | Jenkins et al. |
| 4,393,723 A | 7/1983 | Brand |
| 4,430,079 A | 2/1984 | Thill et al. |
| 4,465,478 A | 8/1984 | Sabelman et al. |
| 4,470,317 A | 9/1984 | Sabloewski et al. |
| 4,493,704 A | 1/1985 | Beard et al. |
| 4,498,904 A | 2/1985 | Turner et al. |
| 4,515,584 A | 5/1985 | Abe et al. |
| 4,568,335 A | 2/1986 | Updike et al. |
| 4,585,439 A | 4/1986 | Michel |
| 4,634,431 A | 1/1987 | Whitney et al. |
| 4,676,122 A | 6/1987 | Szabo et al. |
| 4,749,109 A | 6/1988 | Kamen |
| 4,812,724 A | 3/1989 | Langer et al. |
| 4,833,379 A | 5/1989 | Kaibel et al. |
| 4,838,860 A | 6/1989 | Groshong et al. |
| 4,865,591 A | 9/1989 | Sams |
| 4,871,351 A | 10/1989 | Feingold |
| 4,883,472 A | 11/1989 | Michel |
| 4,893,291 A | 1/1990 | Bick et al. |
| 4,898,578 A | 2/1990 | Rubalcaba |
| 4,919,596 A | 4/1990 | Slate et al. |
| 4,936,833 A | 6/1990 | Sams |
| 4,950,246 A | 8/1990 | Muller |
| 4,973,318 A | 11/1990 | Holm |
| 4,988,337 A | 1/1991 | Ito |
| 4,994,033 A | 2/1991 | Shockey et al. |
| 5,000,744 A | 3/1991 | Hoffman et al. |
| 5,002,537 A | 3/1991 | Hoffman et al. |
| 5,064,098 A | 11/1991 | Hutter et al. |
| 5,078,698 A | 1/1992 | Stiehl et al. |
| 5,104,388 A | 4/1992 | Quackenbush |
| 5,112,317 A | 5/1992 | Michel |
| 5,113,869 A | 5/1992 | Nappholz et al. |
| 5,114,406 A | 5/1992 | Gabriel et al. |
| 5,135,485 A | 8/1992 | Cohen et al. |
| 5,163,904 A | 11/1992 | Lampropoulos et al. |
| 5,176,646 A | 1/1993 | Kuroda |
| 5,207,752 A | 5/1993 | Sorenson et al. |
| 5,221,268 A | 6/1993 | Barton et al. |
| 5,226,342 A | 7/1993 | Panin |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,292,976 A | 3/1994 | Dessau et al. |
| 5,295,976 A | 3/1994 | Harris |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,368,572 A | 11/1994 | Shirota |
| 5,370,629 A | 12/1994 | Michel et al. |
| 5,378,233 A | 1/1995 | Haber et al. |
| 5,383,856 A | 1/1995 | Bersin |
| 5,383,865 A | 1/1995 | Michel |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A | 1/1996 | Gabriel et al. |
| 5,492,534 A | 2/1996 | Athayde et al. |
| 5,496,286 A | 3/1996 | Stiehl et al. |
| 5,505,697 A | 4/1996 | McKinnon, Jr. et al. |
| 5,505,704 A | 4/1996 | Pawelka et al. |
| 5,536,249 A | 7/1996 | Castellano et al. |
| 5,546,932 A | 8/1996 | Galli |
| 5,549,575 A | 8/1996 | Giambatista et al. |
| 5,573,729 A | 11/1996 | Belgardt et al. |
| 5,582,598 A | 12/1996 | Chanoch |
| 5,584,815 A | 12/1996 | Pawelka et al. |
| 5,591,136 A | 1/1997 | Gabriel |
| 5,593,390 A | 1/1997 | Castellano et al. |
| 5,599,314 A | 2/1997 | Neill |
| 5,611,783 A | 3/1997 | Mikkelsen |
| 5,611,784 A | 3/1997 | Barresi et al. |
| 5,626,566 A | 5/1997 | Petersen et al. |
| 5,628,309 A | 5/1997 | Brown |
| 5,637,095 A | 6/1997 | Nason et al. |
| 5,645,052 A | 7/1997 | Kersey |
| 5,662,612 A | 9/1997 | Niehoff |
| 5,674,204 A | 10/1997 | Chanoch |
| 5,679,111 A | 10/1997 | Hertman et al. |
| 5,681,285 A | 10/1997 | Ford et al. |
| 5,685,864 A | 11/1997 | Shanley et al. |
| 5,688,251 A | 11/1997 | Chanoch |
| 5,709,662 A | 1/1998 | Olive et al. |
| 5,716,990 A | 2/1998 | Bagshawe et al. |
| 5,720,733 A | 2/1998 | Brown |
| 5,725,508 A | 3/1998 | Chanoch et al. |
| 5,728,074 A | 3/1998 | Castellano et al. |
| 5,728,559 A | 3/1998 | Nilsson et al. |
| 5,741,211 A | 4/1998 | Renirie et al. |
| 5,743,889 A | 4/1998 | Sams |
| 5,755,692 A | 5/1998 | Manicom |
| 5,782,633 A | 7/1998 | Mühlbauer |
| 5,807,334 A | 9/1998 | Hodosh et al. |
| 5,814,022 A | 9/1998 | Antanavich et al. |
| 5,820,602 A | 10/1998 | Kovelman et al. |
| 5,823,998 A | 10/1998 | Yamagata |
| 5,827,232 A | 10/1998 | Chanoch |
| 5,843,036 A | 12/1998 | Olive et al. |
| 5,879,360 A | 3/1999 | Crankshaw |
| 5,879,630 A | 3/1999 | Lescouzeres et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelson |
| 5,989,221 A | 11/1999 | Hjertman et al. |
| 5,998,989 A | 12/1999 | Lohberg |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,019,745 A | 2/2000 | Gray |
| 6,033,376 A | 3/2000 | Rockley |
| 6,033,377 A | 3/2000 | Rasmussen et al. |
| 6,036,675 A | 3/2000 | Thorne et al. |
| 6,048,336 A | 4/2000 | Gabriel |
| 6,074,372 A | 6/2000 | Hansen et al. |

| | | | | | | |
|---|---|---|---|---|---|---|
| 6,083,197 | A | 7/2000 | Umbaugh | 2002/0020654 A1 | 2/2002 | Eilersen |
| 6,086,567 | A | 7/2000 | Kirchhofer et al. | 2002/0049415 A1 | 4/2002 | Fukuda |
| 6,096,010 | A | 8/2000 | Walters | 2002/0052578 A1 | 5/2002 | Moller |
| 6,110,148 | A | 8/2000 | Brown et al. | 2002/0077852 A1 | 6/2002 | Ford et al. |
| 6,110,149 | A | 8/2000 | Klitgaard et al. | 2002/0107486 A1 | 8/2002 | Munk |
| 6,129,080 | A | 10/2000 | Pitcher et al. | 2002/0120235 A1 | 8/2002 | Enggaard |
| 6,146,361 | A | 11/2000 | DiBiasi et al. | 2002/0165500 A1 | 11/2002 | Bechtold et al. |
| 6,159,161 | A | 12/2000 | Hodosh | 2002/0173752 A1 | 11/2002 | Polzin |
| 6,161,364 | A | 12/2000 | Kolberg | 2002/0188250 A1 | 12/2002 | Landau et al. |
| 6,193,698 | B1 | 2/2001 | Kirchhofer et al. | 2003/0009133 A1 | 1/2003 | Ramey |
| 6,221,046 | B1 | 4/2001 | Burroughs et al. | 2003/0039679 A1 | 2/2003 | Duirs |
| 6,221,053 | B1 | 4/2001 | Walters et al. | 2003/0073954 A1 | 4/2003 | Moberg et al. |
| 6,231,540 | B1 | 5/2001 | Smedegaard | 2003/0114800 A1 | 6/2003 | Veasey et al. |
| 6,235,004 | B1 | 5/2001 | Steenfeldt-Jensen et al. | 2003/0172924 A1 | 9/2003 | Staniforth et al. |
| 6,245,046 | B1 | 6/2001 | Sibbitt | 2003/0176871 A1 | 9/2003 | Pavlov et al. |
| 6,248,090 | B1 | 6/2001 | Jensen et al. | 2003/0216663 A1 | 11/2003 | Willuhn et al. |
| 6,248,095 | B1 | 6/2001 | Giambatista et al. | 2003/0233075 A1 | 12/2003 | Huegli et al. |
| 6,258,062 | B1 | 7/2001 | Thielen et al. | 2004/0010204 A1 | 1/2004 | Weber et al. |
| 6,268,722 | B1 | 7/2001 | Kogure et al. | 2004/0024361 A1 | 2/2004 | Fago |
| 6,269,340 | B1 | 7/2001 | Ford et al. | 2004/0051368 A1 | 3/2004 | Caputo et al. |
| 6,277,097 | B1 | 8/2001 | Mikkelsen et al. | 2004/0059299 A1 | 3/2004 | Moller |
| 6,277,098 | B1 | 8/2001 | Klitmose et al. | 2004/0108339 A1 | 6/2004 | Hansen et al. |
| 6,281,225 | B1 | 8/2001 | Hearst et al. | 2004/0158304 A1 | 8/2004 | Cory et al. |
| 6,283,941 | B1 | 9/2001 | Schoenfeld et al. | 2004/0171983 A1 | 9/2004 | Sparks et al. |
| 6,287,283 | B1 | 9/2001 | Ljunggreen et al. | 2004/0186431 A1 | 9/2004 | Graf et al. |
| 6,302,869 | B1 | 10/2001 | Klitgaard | 2004/0207385 A1 | 10/2004 | Gafner et al. |
| 6,312,413 | B1 | 11/2001 | Jensen et al. | 2004/0210199 A1 | 10/2004 | Atterbury et al. |
| 6,340,357 | B1 | 1/2002 | Poulsen et al. | 2004/0230157 A1 | 11/2004 | Perry et al. |
| 6,364,860 | B1 | 4/2002 | Steck et al. | 2004/0236282 A1 | 11/2004 | Braithwaite |
| 6,379,339 | B1 | 4/2002 | Klitgaard et al. | 2004/0249348 A1 | 12/2004 | Wimpenny et al. |
| 6,383,167 | B2 | 5/2002 | Kirchhofer | 2004/0260247 A1 | 12/2004 | Veasey et al. |
| 6,391,005 | B1 | 5/2002 | Lum et al. | 2004/0267207 A1 | 12/2004 | Veasey et al. |
| 6,419,661 | B1 | 7/2002 | Kuhr et al. | 2004/0267208 A1 | 12/2004 | Veasey et al. |
| 6,514,230 | B1 | 2/2003 | Munk et al. | 2005/0004529 A1 | 1/2005 | Veasey et al. |
| 6,537,251 | B2 | 3/2003 | Klitmose | 2005/0019400 A1 | 1/2005 | Deveney et al. |
| 6,547,755 | B1 | 4/2003 | Lippe et al. | 2005/0033244 A1 | 2/2005 | Veasey et al. |
| 6,547,763 | B2 | 4/2003 | Steenfeldt-Jensen et al. | 2005/0055011 A1 | 3/2005 | Enggaard |
| 6,547,764 | B2 | 4/2003 | Larsen et al. | 2005/0197625 A1 | 9/2005 | Haueter et al. |
| 6,562,011 | B1 | 5/2003 | Buch-Rasmussen et al. | 2005/0205083 A1 | 9/2005 | Staniforth et al. |
| 6,569,126 | B1 | 5/2003 | Poulsen et al. | 2005/0209570 A1 | 9/2005 | Møller |
| 6,582,404 | B1 | 6/2003 | Klitgaard et al. | 2005/0268915 A1 | 12/2005 | Wassenaar et al. |
| 6,585,698 | B1 | 7/2003 | Packman et al. | 2006/0118612 A1 | 6/2006 | Christoffersen et al. |
| 6,599,272 | B1 | 7/2003 | Hjertman et al. | 2006/0258988 A1 | 11/2006 | Keitel et al. |
| 6,605,067 | B1 | 8/2003 | Larsen | 2006/0264838 A1 | 11/2006 | Volckmann |
| 6,613,019 | B2 | 9/2003 | Munk | 2007/0093761 A1 | 4/2007 | Veasey |
| 6,663,602 | B2 | 12/2003 | Moller | 2007/0244445 A1 | 10/2007 | Moller |
| 6,666,849 | B1 | 12/2003 | Marshall et al. | 2008/0065026 A1 | 3/2008 | Moller |
| 6,673,033 | B1 | 1/2004 | Sciulli et al. | 2008/0221530 A1 | 9/2008 | Glejbol et al. |
| 6,692,472 | B2 | 2/2004 | Hansen et al. | 2008/0281275 A1 | 11/2008 | Moller |
| 6,699,224 | B2 | 3/2004 | Kirchhofer et al. | 2009/0043264 A1 | 2/2009 | Glejbol et al. |
| 6,716,198 | B2 | 4/2004 | Larsen | 2009/0062748 A1 | 3/2009 | Moller et al. |
| 6,726,661 | B2 | 4/2004 | Munk et al. | | | |
| 6,752,798 | B2 | 6/2004 | McWethy et al. | FOREIGN PATENT DOCUMENTS | | |
| 6,770,288 | B2 | 8/2004 | Duirs | DE | 3048135 | 7/1982 |
| 6,796,970 | B1 | 9/2004 | Klitmose et al. | DE | 3236374 | 4/1984 |
| 6,852,404 | B2 | 2/2005 | Kuwajima et al. | DE | 36 09 555 | 9/1987 |
| 6,887,238 | B2 | 5/2005 | Jahns et al. | DE | 3638984 | 5/1988 |
| 6,893,415 | B2 | 5/2005 | Madsen et al. | DE | 3923079 | 1/1991 |
| 6,899,698 | B2 | 5/2005 | Sams | DE | 4223958 | 1/1993 |
| 6,899,699 | B2 | 5/2005 | Enggaard | DE | 4419235 | 12/1995 |
| 6,945,961 | B2 | 9/2005 | Miller et al. | DE | 19503230 | 8/1996 |
| 7,008,399 | B2 | 3/2006 | Larsen et al. | DE | 29513214 | 2/1997 |
| 7,080,936 | B1 | 7/2006 | Simpson | DE | 19723647 | 12/1998 |
| 7,090,662 | B2 | 8/2006 | Wimpenny et al. | DE | 19838760 | 4/2000 |
| 7,094,221 | B2 | 8/2006 | Veasey et al. | DE | 29907880 | 9/2000 |
| 7,104,972 | B2 | 9/2006 | Moller et al. | DE | 10103287 | 8/2001 |
| 7,133,329 | B2 | 11/2006 | Skyggebjerg et al. | DE | 10201875 | 5/2003 |
| 7,175,055 | B2 | 2/2007 | Hansen et al. | DE | 10229122 | 2/2004 |
| 7,195,609 | B2 | 3/2007 | Huegli | DE | 20317377 | 4/2005 |
| 7,195,616 | B2 | 3/2007 | Diller et al. | DE | 102004046003 | 3/2006 |
| 7,241,278 | B2 | 7/2007 | Moller | DK | 200100240 | 2/2001 |
| 7,500,966 | B2 | 3/2009 | Hommann | DK | 2005/00116 | 6/2005 |
| 7,678,084 | B2 * | 3/2010 | Judson et al. ............... 604/187 | EP | 15617 | 9/1980 |
| 7,704,238 | B2 | 4/2010 | Diller et al. | EP | 017318 | 10/1980 |
| 2001/0034506 | A1 | 10/2001 | Hirschman et al. | EP | 0064858 | 11/1982 |
| 2001/0053893 | A1 | 12/2001 | Larsen | EP | 327810 | 8/1989 |
| 2002/0002326 | A1 | 1/2002 | Causey, III et al. | EP | 338806 | 10/1989 |
| 2002/0007154 | A1 | 1/2002 | Hansen et al. | EP | 0362484 | 4/1990 |
| 2001/0016571 | A1 | 2/2002 | Kirchhofer et al. | EP | 387854 | 9/1990 |

| | | | | | |
|---|---|---|---|---|---|
| EP | 422482 | 4/1991 | RU | 2111019 | 5/1997 |
| EP | 608313 | 9/1991 | RU | 2091087 | 9/1997 |
| EP | 454331 | 10/1991 | RU | 2212254 | 9/2003 |
| EP | 327910 | 4/1992 | WO | WO8502256 | 5/1985 |
| EP | 498737 | 8/1992 | WO | WO 87/02895 | 5/1987 |
| EP | 879610 | 8/1992 | WO | WO 89/07463 | 8/1989 |
| EP | 0513128 | 11/1992 | WO | WO 90/09202 | 8/1990 |
| EP | 554996 | 8/1993 | WO | 9110460 A1 | 7/1991 |
| EP | 615762 | 3/1994 | WO | WO 91/10460 | 7/1991 |
| EP | 594349 | 4/1994 | WO | WO9110677 | 7/1991 |
| EP | 513128 | 7/1995 | WO | WO 9114467 | 10/1991 |
| EP | 0673482 | 9/1995 | WO | WO9301573 | 1/1993 |
| EP | 679440 | 11/1995 | WO | WO 9303780 | 3/1993 |
| EP | 702970 | 3/1996 | WO | WO 93/07922 | 4/1993 |
| EP | 1000631 | 10/1997 | WO | WO 9412228 | 6/1994 |
| EP | 0 608 343 B1 | 12/1997 | WO | WO9524233 | 9/1995 |
| EP | 554995 | 12/1997 | WO | WO 96/07443 | 3/1996 |
| EP | 295075 | 12/1998 | WO | WO 96/26754 | 9/1996 |
| EP | 897728 | 2/1999 | WO | WO 96/32973 | 10/1996 |
| EP | 0937471 | 8/1999 | WO | WO 96/38190 | 12/1996 |
| EP | 0937472 | 8/1999 | WO | WO 97/07841 | 3/1997 |
| EP | 0937476 | 8/1999 | WO | WO 9710865 | 3/1997 |
| EP | 1003581 | 8/1999 | WO | WO9730742 | 8/1997 |
| EP | 1351732 | 1/2001 | WO | WO9734919 | 9/1997 |
| EP | 1074273 | 2/2001 | WO | WO 97/36626 | 10/1997 |
| EP | 1095668 | 5/2001 | WO | WO 98/10813 | 3/1998 |
| EP | 0747391 | 3/2004 | WO | WO 98/56436 | 12/1998 |
| EP | 1462134 A1 | 9/2004 | WO | WO98/57688 | 12/1998 |
| EP | 937476 | 1/2005 | WO | WO9907425 | 2/1999 |
| EP | 1541185 | 6/2005 | WO | WO 99/16487 | 4/1999 |
| EP | 1557163 | 7/2005 | WO | WO9915214 | 4/1999 |
| EP | 1557189 | 7/2005 | WO | WO 9916487 | 4/1999 |
| EP | 1 568 389 A1 | 8/2005 | WO | WO 9921598 | 5/1999 |
| EP | 1304129 | 11/2005 | WO | WO 9938554 | 8/1999 |
| EP | 1610848 | 1/2006 | WO | WO 9948546 | 9/1999 |
| EP | 1645301 | 4/2006 | WO | WO9965548 | 12/1999 |
| EP | 1723977 | 11/2006 | WO | WO0037129 | 6/2000 |
| EP | 1728529 | 12/2006 | WO | WO 00/51668 | 9/2000 |
| EP | 1782853 | 5/2007 | WO | WO 01/10484 | 2/2001 |
| EP | 1819382 | 8/2007 | WO | WO 01/19434 | 3/2001 |
| EP | 2000161 | 12/2008 | WO | WO0126710 | 4/2001 |
| FR | 2583291 | 12/1986 | WO | WO 01/30425 | 5/2001 |
| FR | 2622457 | 5/1989 | WO | WO0172361 | 10/2001 |
| FR | 2697434 | 5/1994 | WO | WO 0195959 | 12/2001 |
| FR | 2740345 | 4/1997 | WO | WO0205876 | 1/2002 |
| FR | 2 767 479 | 2/1999 | WO | WO0224257 | 3/2002 |
| FR | 2857654 | 1/2005 | WO | WO 02/053214 | 7/2002 |
| GB | 664044 A | 1/1952 | WO | WO02064196 | 8/2002 |
| GB | 2091107 | 7/1982 | WO | WO 02/076535 | 10/2002 |
| GB | 2153445 | 8/1985 | WO | WO 02076536 | 10/2002 |
| GB | 2229497 | 9/1990 | WO | WO 02/092153 | 11/2002 |
| GB | 2309644 | 8/1997 | WO | 03/057286 A1 | 7/2003 |
| GB | 0007071.4 | 3/2000 | WO | WO03057283 | 7/2003 |
| IN | 165367 | 3/1986 | WO | WO03063680 | 8/2003 |
| JP | 56-163486 | 12/1981 | WO | WO9733638 | 9/2003 |
| JP | 57-000033 | 1/1982 | WO | WO 03/080160 | 10/2003 |
| JP | 01-100495 | 4/1989 | WO | WO03099357 | 12/2003 |
| JP | 64-035671 | 6/1989 | WO | WO 2004/002556 | 1/2004 |
| JP | 02-126184 | 5/1990 | WO | WO 2004/007002 A1 | 1/2004 |
| JP | 02-182267 | 7/1990 | WO | WO 2004004825 | 1/2004 |
| JP | 4-224764 | 8/1992 | WO | WO 2004/024218 | 3/2004 |
| JP | 4-507059 | 12/1992 | WO | WO 2004/028598 | 4/2004 |
| JP | 05-337179 | 12/1993 | WO | WO 2004/035113 | 4/2004 |
| JP | 06-055644 | 1/1994 | WO | WO 2006/045529 | 4/2004 |
| JP | 7-500039 | 3/1994 | WO | WO 2004/078239 | 9/2004 |
| JP | 06-034825 | 10/1994 | WO | WO 2004/078240 | 9/2004 |
| JP | 06-296691 | 10/1994 | WO | WO 2004/078241 | 9/2004 |
| JP | 7-502678 | 3/1995 | WO | WO 2004078242 | 9/2004 |
| JP | 09166474 | 6/1997 | WO | WO2004080306 | 9/2004 |
| JP | 3017167 | 11/1999 | WO | WO2004084795 | 10/2004 |
| JP | 2000237308 | 9/2000 | WO | WO2004095379 | 11/2004 |
| JP | 2002503122 A | 1/2002 | WO | WO 2005018721 | 3/2005 |
| JP | 2003284777 | 10/2003 | WO | WO 2005037352 | 4/2005 |
| JP | 2004-503303 | 2/2004 | WO | WO 2005/046770 | 5/2005 |
| JP | 2004503303 A | 2/2004 | WO | WO2005089835 | 9/2005 |
| JP | 2004-516895 | 6/2004 | WO | WO2005097233 | 10/2005 |
| JP | 2004533285 A | 11/2004 | WO | WO2005097240 | 10/2005 |
| JP | 2006250582 | 9/2006 | WO | WO2006039930 | 4/2006 |
| JP | 2007-509662 | 4/2007 | WO | WO 2006/045528 | 5/2006 |

| WO | WO2006045425 | 5/2006 |
| WO | WO2006045525 | 5/2006 |
| WO | WO 2006/069454 | 7/2006 |
| WO | WO2006076921 | 7/2006 |
| WO | WO2006116997 | 11/2006 |
| WO | WO 2006/128794 | 12/2006 |
| WO | WO 2007/030957 | 3/2007 |
| WO | WO2007041843 | 4/2007 |
| WO | WO2007107558 | 9/2007 |
| WO | WO2007107561 | 9/2007 |
| WO | WO 2007/134954 | 11/2007 |
| WO | WO 2008/037801 | 4/2008 |
| WO | WO2008057223 | 5/2008 |

OTHER PUBLICATIONS

Final Rejection mailed on Sep. 29, 2009 in U.S. Appl. No. 11/911,869, filed on Oct. 18, 2007 by Glejbol et al.
Non-final Rejection mailed on Jan. 8, 2009 in U.S. Appl. No. 11/911,869, filed on Oct. 18, 2007 by Glejbol et al.
Notice of Allowance mailed on Apr. 23, 2007 in U.S. Appl. No. 10/667,040, filed on Sep. 22, 2003 by Moller et al.
Final Rejection mailed on Nov. 5, 2009 in U.S. Appl. No. 11/122,289, filed on May 4, 2005 by Moller et al.
Non-final Rejection mailed on Dec. 15, 2008 in U.S. Appl. No. 11/122,289, filed on May 4, 2005 by Moller et al.
Non-final Rejection mailed on Mar. 17, 2008 in U.S. Appl. No. 11/122,289, filed on May 4, 2005 by Moller et al.
Final Rejection mailed on Nov. 5, 2009 in U.S. Appl. No. 11/765,789, filed on Jun. 20, 2007 by Moller et al.
Non-final Rejection mailed on Dec. 17, 2008 in U.S. Appl. No. 11/765,789, filed on Jun. 20, 2007 by Moller et al.
Non-final Rejection mailed on Mar. 14, 2008 in U.S. Appl. No. 11/765,789, filed on Jun. 20, 2007 by Moller et al.
Final Rejection mailed on Jan. 15, 2010 in U.S. Appl. No. 11/930,926, filed on Oct. 31, 2007 by Moller et al.
Non-final Rejection mailed on Apr. 2, 2009 in U.S. Appl. No. 11/930,926, filed on Oct. 31, 2007 by Moller et al.
Abandonment mailed on Nov. 6, 2009 in U.S. Appl. No. 11/911,871, filed on Oct. 18, 2007 by Glejbol et al.
Non-final Rejection mailed on Apr. 1, 2009 in U.S. Appl. No. 11/911,871, filed on Oct. 18, 2007 by Glejbol et al.
Non-final Rejection mailed on Jun. 8, 2010 in U.S. Appl. No. 12/571,721, filed on Oct. 1, 2009 by Glejbol et al.
English Abstract of DE10201875 Published May 22, 2003.
English Abstract of DE102004046003 Published Mar. 30, 2006.
English Abstract of DE19503230 Published Aug. 8, 1996.
English Abstract of DE 19838760 Published April 20, 2000.
English Abstract of DE29513214 Published Feb. 13, 1997.
English Abstract of DE3048135 Published Jul. 15, 1982.
English Abstract of DE3236374 Published Apr. 5, 1984.
English Abstract of DE3923079 Published Jan. 24, 1991.
English Abstract of EP387854 Published Sep. 19, 1990.
English Abstract of EP422482 Published Apr. 17, 1991.
English Abstract of FR2622457 Published May 5, 1989.
English Abstract of FR 2697434 Published May 6, 1994.
English Abstract of FR2740345 Published Apr. 30, 1997.
English Abstract of IN165367 Published Mar. 20, 1986.
English Abstract of JP01-100495 Published Apr. 18, 1989.
English Abstract of JP02-126184 Published May 15, 1990.
English Abstract of JP02-182267 Published Jul. 16, 1990.
English Abstract of JP57-000033 Published Jan. 5, 1982.
English Abstract of JP64-035671 Published Jun. 2, 1989.
English Abstract for JP 2000237308 Published Sep. 5, 2000.
English Abstract for JP 2003284777 Published Oct. 7, 2003.
English Abstract of JP06-034825 Published Oct. 2, 1994.
English Abstract of JP06-055644 Published Jan. 3, 1994.
Machine Translation of JP09166474 Published Jun. 24, 1997.
English Abstract of JP2006250582 Published Sep. 21, 2006.
English Abstract of JP3017167 Published Nov. 30, 1999.
English Abstract of JP56-163486 Published Dec. 16, 1981.
English Abstract of JP 7-500039 Published Mar. 14, 1994.
Annersten, M. et al., Insulin Pens Dribble From the Tip of the Needle After Injection, Practical Diabetes Int., vol. 17(4), pp. 109111 (2000).
Beckmann, Sensors, Memory, Circuits, Polyapply Newsletter, vol. 1(3), (2006).
Chia Kai Su et al, Process Biochemistry, 2006, vol. 41, Part 2, pp. 257-263.
Common Insulin Injection Challenges: http://www.bd.com/us/diabetes/page.aspx?cat=7001&id=7265.
Dennison, Clive et al, Protein Expression and Purification, 2004, vol. 11, Part 2, pp. 149-161.
Fransson et al, Pharmaceutical Research, 1997, vol. 14, Part 5, pp. 606-612.
Gnanalingham, M.G. et al., Accuracy and Reproducibility of Low Dose Insulin Administration Using Pen-Injectors and Syringes, Downloaded From ADC.BMJ.COM on January 9, 2008.
Leonil et al, Enzyme and Microbiol Technology, 1994, vol. 16, Part 7, pp. 591-595.
Owen Mumford Product Range.
Paule, B.J.A. et al, Protein Expression and Purification, 2004, vol. 34, Part 2, pp. 311-316.
Search Report Issued in Connection With PCT Appln. No. PCT/EP2007/052630, Mailed Nov. 12, 2007.
Search Report Issued in Connection With European Application No. 06005599.3, Mailed Oct. 4, 2006.
Search Report Issued in Connection With PCT Application No. PCT/EP2007/052633, Mailed Feb. 20, 2008.
Search Report Issued in Connection With European Appln No. 06005602.5, Mailed Oct. 16, 2006.
Trankler, Hans-Rolf, R. Oldenbourg, Verlag, Munchen, Wien.
Notice of Opposition by Owen Mumford (UK).
Notice of Opposition by Genentech (USA).
Notice of Opposition by Techpharma (CH) Including English Translation.
Opposition in Related European Patent Application EP 02711784.5 of Sep. 19, 2008.
Validity Opinion by the UK PTO.
Office Action Mailed Mar. 17, 1999 in U.S. Appl. No. 08/973,109, filed Jun. 3, 1996 by Klitmose.
Notice of Allowance Mailed Oct. 25, 1999 in U.S. Appl. No. 08/973,109, filed Jun. 3, 1996 by Klitmose.
Office Action Mailed Apr. 26, 1999 in U.S. Appl. No. 09/090,144, filed Jun. 4, 1998 by Klitmose.
Final Action Mailed Dec. 20, 1999 in U.S. Appl. No. 09/090,114, filed Jun. 4, 1998 by Klitmose.
Notice of Allowance Mailed Apr. 6, 2004 in U.S. Appl. No. 09/090,144, filed Jun. 4, 1998 by Klitmose.
Office Action Mailed on Sep. 15, 2004 in U.S. Appl. No. 10/646,295, filed Aug. 22, 2003 by Hansen et al.
Final Office Action Mailed on Feb. 8, 2005 in U.S. Appl. No. 10/646,295, filed Aug. 22, 2003 by Hansen et al.
Advisory Action Mailed Jul. 1, 2005 in U.S. Appl. No. 10/646,295, filed Aug. 22, 2003 by Hansen et al.
Office Action Mailed on Aug. 29, 2005 in U.S. Appl. No. 10/646,295, filed Aug. 22, 2003 by Hansen et al.
Final Office Action Mailed on Apr. 14, 2006 in U.S. Appl. No. 10/646,295, filed Aug. 22, 2003 by Hansen et al.
Notice of Allowance Mailed on Sep. 26, 2006 in U.S. Appl. No. 10/646,295, filed Aug. 22, 2003 by Hansen et al.
Non-Final Office Action Mailed Aug. 27, 2002 in U.S. Appl. No. 09/882,536, filed Jun. 14, 2001 by Moller et al.
Notice of Allowance Mailed Jun. 17, 2003 in U.S. Appl. No. 09/882,536, filed Jun. 4, 2001 by Moller et al.
Advisory Action Mailed on Mar. 25, 2010 in U.S. Appl. No. 11/122,289, filed on May 4, 2005 by Moller et al.
Final Action Mailed on Jan. 15, 2010 in U.S. Appl. No. 11/930,926, filed Oct. 31, 2007 by Moller et al.
Office Action Mailed on Apr. 2, 2009 in 11/931,010, filed on Oct. 31, 2007 by Moller et al.
Final Office Action Mailed on Jan. 15, 2010 in 11/931,010, filed on Oct. 31, 2007 by Moller et al.
Office Action Mailed Jul. 20, 2010 in U.S. Appl. No. 12/300,675, filed May 3, 2007 by Moller et al.
Non-Final Rejection of Oct. 7, 2008 in U.S. Appl. No. 10/508,104 (US Patent No. 7,678,084; Issue Date Mar. 16, 2010) Filed Sep. 15, 2004; First Named Inventor: Jared Alden Judson.

Non-Final Rejection of Mar. 19, 2009 in U.S. Appl. No. 10/508,104 (US Patent No. 7,678,084; Issue Date March 16, 2010) Filed Sep. 15, 2004; First Named Inventor: Jared Alden Judson.

Final Rejection mailed on Dec. 13, 2010 in U.S. Appl. No. 12/571,721, filed on Oct. 1, 2009 by Glejbol et al.

Answer in *Novo Nordisk A/S v. Sanofi-Aventis U.S. LLC and Sanofi-Aventis* downloaded from PACER on Feb. 29, 2008.

Complaint in *Novo Nordiks A/S v. Sanofi-Aventis U.S. LLC and Sanofi-Aventis* downloaded from PACER on Feb. 29, 2008.

Declaration of *Benard Sams in Novo Nordisk A/S v. Sanofi-Aventis U.S. LLC and Sanofi-Aventis* downloaded from PACER on Feb. 29, 2008.

International Search Report and Written Opinion issued in connection with counterpart PCT Application No. PCT/EP2006/061747 mailed Sep. 29 2006.

International Search Report and Written Opinion issued in connection with counterpart PCT Application No. PCT/EP2006/061748 mailed Aug. 10 2006.

May 17, 2002 Office Action in 09768760 and accompanying 892 and 1149 forms.

Opinion of US District Court for the District of NJ (in *Novo Nordisk A/S v. Sanofi-Aventis U.S. LLC* and *Sanofi-Aventis* Denying motion of a preliminary injunction entered Feb. 20, 2008.

PAIR Print-out of file history of U.S. Appl. No. 10/610,926 which is owned by the same assignee as U.S. Appl. No. 11/765,789.

Search Report issued in connection with counterpart Danish Application No. PA 2005 00588 mailed Feb. 13, 2006.

Search Report issued in connection with counterpart Danish Application No. PA 2005 00589 mailed Feb. 16, 2006.

US Reissue U.S. Appl. No. 10/442,855 File History from PAIR on Feb. 8, 2008.

US Reissue U.S. Appl. No. 10/960,900 File History from PAIR on Feb. 8, 2008.

US Reissue U.S. Appl. No. 11/121,331 File History from PAIR on Feb. 8, 2008.

US Reissue U.S. Appl. No. 11/640,610 File History from PAIR on Feb. 8, 2008.

Written Opinion issued in connection with counterpart PCT Application No. PCT/EP2006/061747 mailed Nov. 8 2006.

Written Opinion issued in connection with counterpart PCT Application No. PCT/EP2006/061748 mailed Nov. 8 2006.

English Abtsract of JP4-507059 Published Dec. 10, 1992.

Abstract of AU2003232576.

* cited by examiner

US 8,361,036 B2

INJECTION DEVICE HAVING A GEARING ARRANGEMENT

CROSS-REFERENCE TO RELATED APPLICATIONS

This application is a 35 U.S.C. §371 national stage application of International Patent Application PCT/EP2007/052177 (published as WO 2007/104697), filed Mar. 8, 2007, which claimed priority of European Patent Application 06004932.7, filed Mar. 10, 2006; this application further claims priority under 35 U.S.C. §119 of U.S. Provisional Application 60/784,775, filed Mar. 22, 2006.

FIELD OF THE INVENTION

The present invention relates to an injection device for delivering a drug to the human body, the injection device being of the kind where a dose setting member is operable to set a desired dose by rotation of the dose setting member. More particularly, the present invention relates to an injection device of the above mentioned kind having a gearing arrangement providing a gearing ratio between an axial movement of an injection button and an axial movement of a piston rod. The injection device of the present invention is particularly suitable for treatment by self-injection of drugs, such as growth hormone or insulin for people with diabetes.

BACKGROUND OF THE INVENTION

Injection devices of the kind where a dose setting member is operable to set a desired dose by rotation of the dose setting member are known in the art. An example of such an injection device is an elongated device also known as an injection pen, due to its resemblance with a pen.

In order to reduce the pressure needed to be applied by a user to cause a set dose to be expelled from an injection device, it is desirable to provide a gearing arrangement in the injection device in order to allow for an injection button to have a larger stroke than a piston.

US 2004/0059299 discloses an injection device having such a gearing arrangement in the form of a gear box. The gear box is fixed in a housing of the injection device in a way that allows the gear box to rotate in the housing but not to be axially displaced relative to the housing. Thus, during dose setting, the gear box rotates along with the dose knob. In order to allow this rotation of the gear box, a relatively large space needs to be accommodated inside the housing, even though the gear box will only occupy a relatively small part of the accommodated space at any given time. Thereby the injection device becomes relatively bulky.

SUMMARY OF THE INVENTION

It is, thus, an object of the invention to provide an injection device with a gearing arrangement as described above, the injection device being more flat than prior art injection devices.

It is a further object of the invention to provide an injection device with a gearing arrangement as described above in which the available space inside a housing of the injection device is utilised to the maximum available extent possible.

It is an even further object of the invention to provide an injection device with a gearing arrangement as described above, the injection device being provided with additional electronics without adding substantially to the total size of the injection device.

It is an even further object of the invention to provide an injection device having a relatively flat appearance.

According to a first aspect of the present invention the above and other objects are fulfilled by providing an injection device comprising:
 a housing,
 a dose setting member being operable to set a dose by rotating said dose setting member relatively to the housing, about a rotational axis,
 a piston rod adapted to cause a set dose to be injected from the injection device,
 an injection button adapted to perform an axial movement, and operable to cooperate with the piston rod in injecting a set dose in such a manner that when the injection button is operated a set dose is caused to be injected by the piston rod,
 a gearing arrangement comprising at least one gear wheel, the gearing arrangement providing a gearing ratio between an axial movement of the injection button and an axial movement of the piston rod,
wherein the gearing arrangement, during setting of a dose, is prevented from rotating along with the dose setting member about the rotational axis, and wherein at least one of the gear wheel(s) has a rotational axis which is non-parallel to the rotational axis of the dose setting member.

In the present context the term 'housing' should be interpreted to mean a substantially closed part surrounding at least some of the other parts of the injection device.

The dose setting member is a part of the injection device being operable to set a desired dose. During setting of a dose the dose setting member is rotated about a rotational axis. The rotational axis is preferably arranged at least substantially along a longitudinal axis of the injection device. The dose setting member preferably is or comprises a rotatable dose knob. The dose setting member preferably forms part of a dose setting mechanism, the dose setting mechanism comprising further parts which are needed in order to set a desired dose, e.g. a dose rod.

The piston rod is adapted to cause a set dose to be injected from the injection device. In doing so, the piston rod cooperates with a piston of a cartridge positioned in the injection device. The piston rod and the piston are preferably in abutment, an axial movement of the piston rod thereby causing an identical axial movement of the piston in the cartridge.

The injection button is operable by a user in such a manner that when the user presses the injection button in an axial direction, the piston rod is also moved axially, thereby causing a set dose to be injected.

The gearing arrangement provides a gearing ratio between an axial movement of the injection button and an axial movement of the piston rod. Thereby the force needed to be applied by the user to the injection button in order to axially move the piston rod sufficiently to cause the set dose to be injected is reduced. The gearing ratio may be 2:1, 3:1 or any other suitable ratio.

When a dose is being set, and the dose setting member is therefore rotated about the rotational axis, the gearing arrangement is prevented from rotating along with the dose setting member about the rotational axis. This is very advantageous because the space accommodated for the gearing arrangement inside the housing can thereby be considerably reduced as compared to an injection device in which the gearing arrangement rotates along with the dose setting member. Thus, this space may be used for other purposes, e.g. for accommodating additional electronics, including a display screen and/or a battery, or the overall size of the injection device may be reduced. It will also be possible to position the gearing arrangement in a specific part of the cross section of the injection device, thereby providing the possibility of designing the injection device with a relatively flat cross section.

It should be noted that the gearing arrangement or part of the gearing arrangement may still be allowed to perform rotational movements as long as such additional rotational movements are not performed about the rotational axis of the dose setting member. For instance, according to the first aspect of the invention, the gearing arrangement comprises one or more gear wheels adapted to perform rotational movements about individual rotational axes. At least one of the gear wheel(s) has a rotational axis which is non-parallel to the rotational axis of the dose setting member.

The injection device may further comprise a dose rod being at least substantially rotationally locked to the dose setting member, and the gearing arrangement may be at least substantially axially fixed to the dose rod in such a manner that the dose rod and the gearing arrangement may perform a relative rotational movement. Since the dose rod is at least substantially locked to the dose setting member it will rotate along with the dose setting member during setting of a dose. The dose rod is preferably arranged in such a manner that it at least substantially coincides with the rotational axis of the dose setting member. In this case the dose rod will rotate about its own longitudinal axis during setting of a dose. Since the dose rod and the gearing arrangement may perform a relative rotational movement, the dose rod is allowed to perform this rotational movement without the gearing arrangement rotating along. However, the gearing arrangement is at least substantially axially fixed to the dose rod, i.e. the gearing arrangement and the dose rod can not be moved relatively to each other in an axial direction. This may, e.g., be achieved by arranging the gearing arrangement in a slide being provided with a pair of holes through which the dose rod is arranged. This construction is very simple and results in a very flat injection device. This is very advantageous.

The gearing arrangement comprises at least one gear wheel. At least one of the gear wheel(s) may have a rotational axis being at least substantially perpendicular to the rotational axis of the dose setting member. Arranging the gear wheel(s) in this manner provides the possibility of making the injection device relatively flat, thereby making it easier to provide the injection device with display means, e.g. for displaying a set dose, the remaining amount of drug left in the cartridge, the kind of drug in the cartridge (e.g. fast acting, slow acting or mix insulin), a diary relating to diabetes treatment, etc.

The injection device may further comprise a crown wheel being operationally coupled to the dose setting member in such a manner that the crown wheel is caused to perform a rotational movement when the dose setting member is operated, said rotational movement being performed about a rotational axis which is non-parallel to the rotational axis of the dose setting member. In this embodiment the crown wheel is preferably coupled to the dose setting member via an extruded gear wheel adapted to rotate along with the dose setting member about the rotational axis of the dose setting member during dose setting. The extruded gear wheel engages the crown wheel which is thereby caused to rotate about a rotational axis being non-parallel to the rotational axis of the dose setting member. The rotational axis of the crown wheel may advantageously be arranged at least substantially perpendicularly to the rotational axis of the dose setting member. The crown wheel may further be operationally connected to a gear wheel in such a manner that when the crown wheel is rotated, the gear wheel is caused to move axially along the piston rod in such a manner that when the desired dose has been set and the injection button is subsequently pushed, the gear wheel will move the piston rod in an axial direction, thereby causing the set dose to be injected from the injection device.

According to a second aspect of the invention the above and other objects are fulfilled by providing an injection device comprising:
  a housing,
  a dose setting member being operable to set a dose by rotating said dose setting member relatively to the housing, about a rotational axis,
  a piston rod adapted to cause a set dose to be injected from the injection device,
  an injection button adapted to perform an axial movement, and operable to cooperate with the piston rod in injecting a set dose in such a manner that when the injection button is operated a set dose is caused to be injected by the piston rod,
  a gearing arrangement providing a gearing ratio between an axial movement of the injection button and an axial movement of the piston rod, said gearing arrangement comprising a driving spindle operationally coupled to the injection button and to the piston rod, the driving spindle being provided with a threaded portion having a first pitch and the piston rod being provided with a threaded portion having a second pitch, wherein the gearing is provided by the threaded portions, the gearing ratio corresponding to the ratio between the first and the second pitch,
wherein the gearing arrangement, during setting of a dose, is prevented from rotating along with the dose setting member about the rotational axis.

It should be noted that a person skilled in the art would readily recognise that any feature described in combination with the first aspect of the invention may also be combined with the second aspect of the invention, and vice versa.

Thus, according to the second aspect, the injection device comprises a driving spindle operationally coupled to the injection button and to the piston rod. The driving spindle is provided with a threaded portion having a first pitch and the piston rod is provided with a threaded portion having a second pitch, and the gearing is provided by the threaded portions, the gearing ratio corresponding to the ratio between the first and the second pitch. Accordingly, the driving spindle forms part of the gearing arrangement.

According to the second aspect of the invention the gearing arrangement is also prevented from rotating along with the dose setting member about the rotational axis of the dose setting member during dose setting. This has already been described in detail above with reference to the first aspect of the invention. In particular, according to the second aspects of the invention, the driving spindle is prevented from rotating along with the dose setting member during dose setting. Thus, the space accommodated for the gearing arrangement inside the housing can be considerably reduced as described above.

In some prior art injection devices comprising a driving spindle, the driving spindle is arranged coaxially with the piston rod. Thereby the cross sectional area of the injection device becomes relatively large, and the cross section will normally be at least substantially circular. Alternatively, the driving spindle and the piston rod may be arranged in parallel, in which case the driving spindle would have to rotate about the rotational axis of the dose setting member, thereby defining a circle with a radius defined by the distance between the driving spindle and the piston rod. According to the second aspect of the invention the driving spindle may define a longitudinal axis being arranged at least substantially parallel to the rotational axis of the dose setting member, and it may be rotatable about its own axis. Thereby it is possible to allow the injection device to be relatively flat, and the advantages described above are thereby achieved.

BRIEF DESCRIPTION OF THE DRAWINGS

The invention will now be further described with reference to the accompanying drawings in which.

DETAILED DESCRIPTION OF THE DRAWINGS

Figure 1:
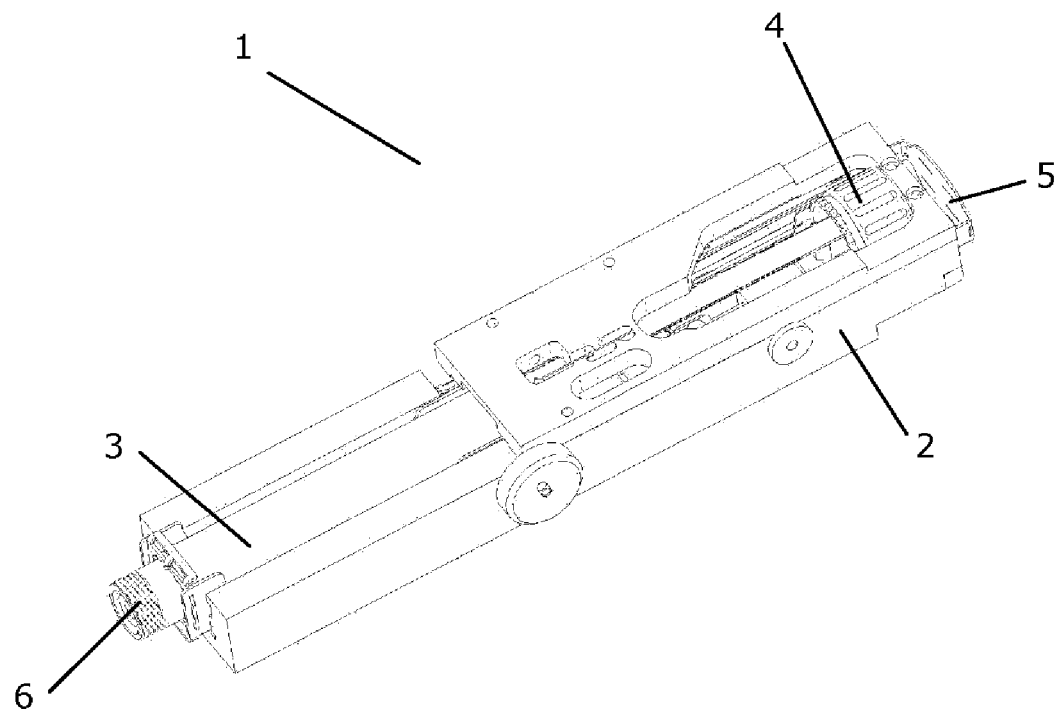
FIGS. 1-5 illustrate an injection device according to a first embodiment of the invention.

FIGS. 1-5 illustrate an injection device 1 according to a first embodiment of the invention. FIG. 1 is a perspective view of the injection device 1. The injection device 1 comprises a housing 2, a cartridge 3 containing a drug to be injected, a dose setting member 4 and an injection button 5. At a distal end 6 of the cartridge 3 it is possible to attach a needle in order to allow the drug of the cartridge 3 to be injected subcutaneously.

The operation of the injection device 1 shown in FIG. 1 will now be described with reference to FIGS. 2-5.

Figure 2:
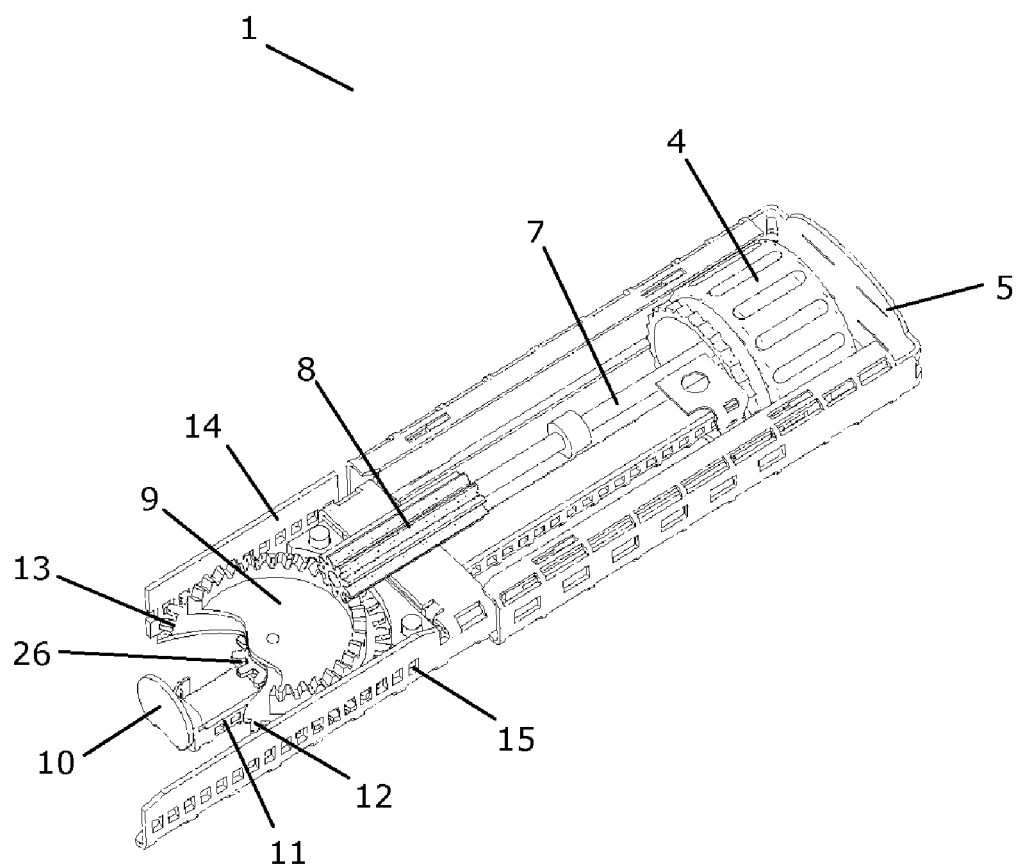

FIG. 2 shows selected parts of the injection device 1, the selected parts being essential for describing the operation of the injection device 1. Additional parts, such as the housing, which are not essential for describing the operation of the injection device 1 have been omitted for the sake of clarity.

The injection device 1 of FIG. 2 comprises a dose setting member 4 connected to a dose rod 7 and to an extruded gear wheel 8. The dose setting member 4, the dose rod 7 and the extruded gear wheel 8 perform a rotational movement about a common rotational axis during dose setting. The rotational axis is defined by the dose rod 7.

The extruded gear wheel 8 engages a crown wheel 9. Thus, when the extruded gear wheel 8 rotates during dose setting, the crown wheel 9 is also caused to rotate. However, the crown wheel 9 rotates about a rotational axis which is arranged substantially perpendicular to the rotational axis of the dose setting member 4. The crown wheel 9 is operationally coupled to a first gear wheel 26 in such a manner that the first gear wheel 26 rotates coaxially along with the crown wheel 9 during dose setting. The first gear wheel 26 is further coupled to a piston rod 10 by means of a set of teeth on the first gear wheel 26 engaging a track 11 on the piston rod 10. Thereby, when the crown wheel 9 and the first gear wheel 26 are rotated during dose setting, the gear arrangement comprising the crown wheel 9, the first gear wheel 26 and a second gear wheel 12 positioned between the crown wheel 9 and the first gear wheel 26 is moved axially relatively to the piston rod 10 due to the connection between the first gear wheel 26 and the piston rod 10. The second gear wheel 12 is provided with a set of teeth 13 which engage a track on a first rack 14 which is substantially fixed relatively to the housing (not shown), and with a track on a second rack 15 which is movable relatively to the housing, but fixed to the injection button 5. As a result, the injection button 5 is moved axially in a proximal direction, i.e. away from the housing, as the gearing arrangement is moved axially. As the second gear wheel 12 moves axially, the peripheral velocity at the point where the second gear wheel 12 engages the first rack 14 will be substantially 0, while the peripheral velocity at the point where the second gear wheel 12 engages the second rack 15 will be substantially twice the axial velocity of the second gear wheel 12.

In FIG. 2 the injection device 1 is in a position in which it is ready for setting a dose. Thus, the injection button 5 is in a position which is as close to the housing as possible. Furthermore, the piston rod 10 is relatively close to the gearing arrangement, indicating that a full cartridge has recently been inserted in the injection device 1.

Figure 3:
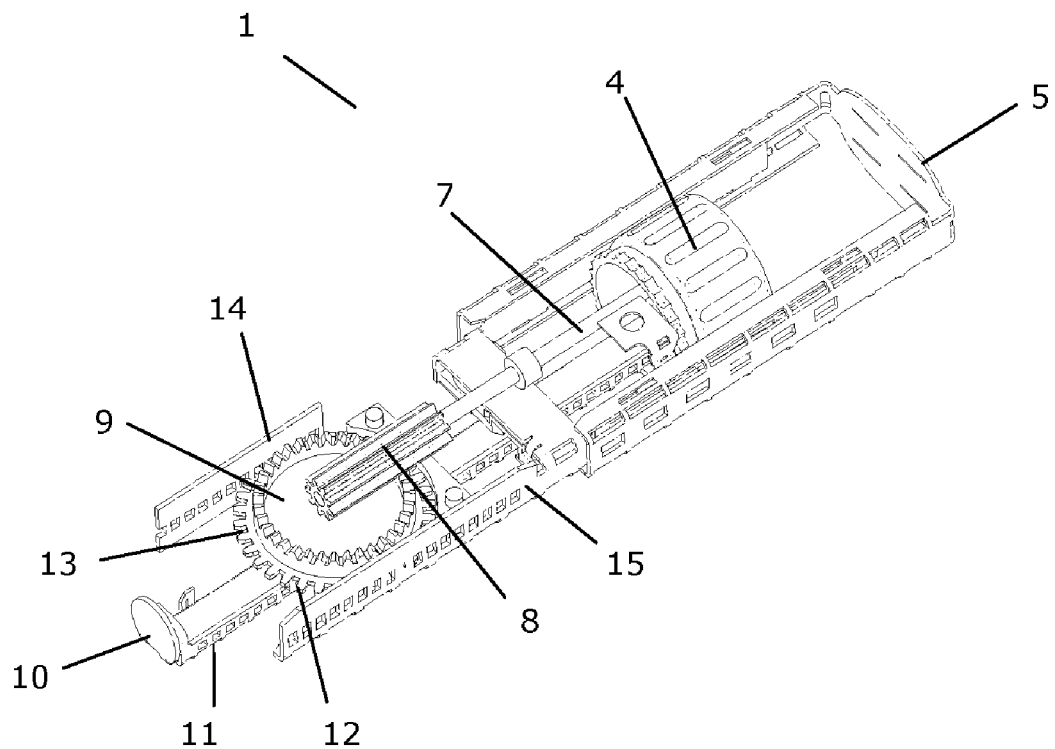

FIG. 3 shows the injection device 1 of FIGS. 1 and 2 in a position in which a desired dose has been set but not yet injected. Comparing FIG. 3 to FIG. 2 it is, thus, clear that the injection button 5 has been moved outwards and the gearing arrangement has been moved axially relatively to the first rack 14, and thereby relatively to the housing, and relatively to the piston rod 10. When the set dose is to be injected, the user pushes the injection button 5 in a distal direction, i.e. towards the housing. Due to the engagement between the track of the second rack 15 and the teeth 13 of the second gear wheel 12, the gearing arrangement will also be moved in a distal direction. However, due to the engagement between the teeth 13 of the second gear wheel 12 and the track of the first rack 14, the second gear wheel 12 is caused to rotate during this axial movement. Accordingly, the distance traveled by the gearing arrangement will be shorter than the distance traveled by the injection button 5, thereby providing a gearing. Due to the engagement between the first gear wheel (not visible) and the track 11 on the piston rod 10, and due to the fact that the first gear wheel is prevented from rotating during injection, the piston rod 10 is caused to move along with the gearing arrangement, thereby causing the set dose to be expelled from the cartridge.

Figure 4:
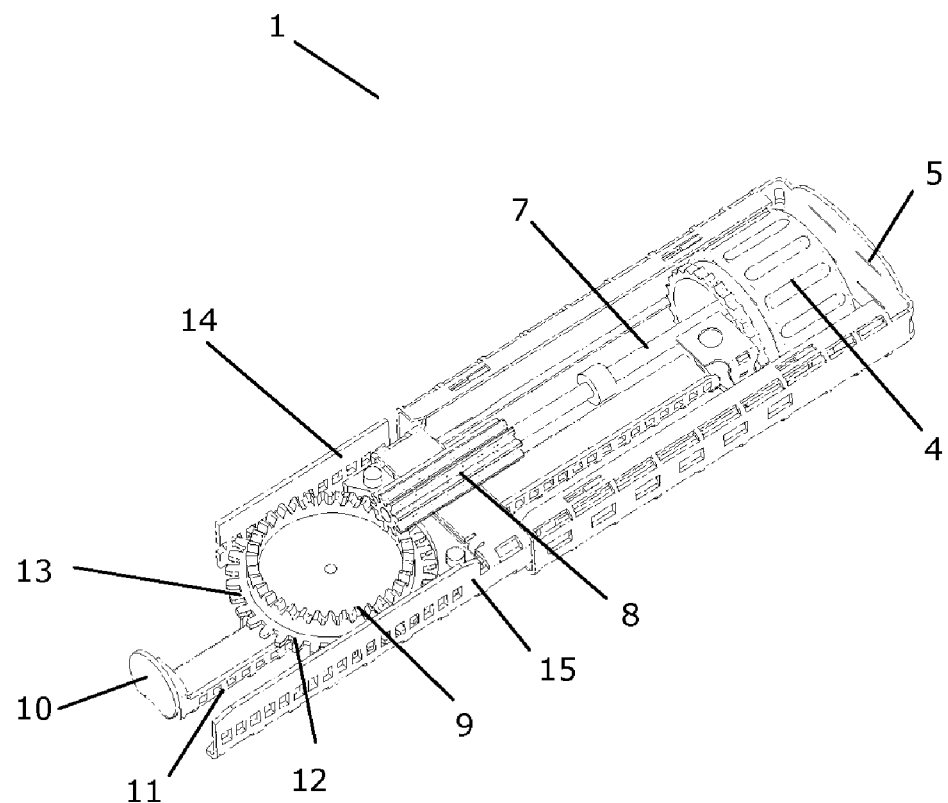

FIG. 4 shows the injection button 1 of FIGS. 1-3 in a position where a set dose has just been injected. Thus, in FIG. 4 the injection button 5 and the gearing arrangement are in the same positions as in FIG. 2. However, the piston rod 10 has been moved axially in a distal direction as compared to the position of the piston rod 10 in FIG. 2, thereby indicating that a dose has been injected from the cartridge.

Figure 5:
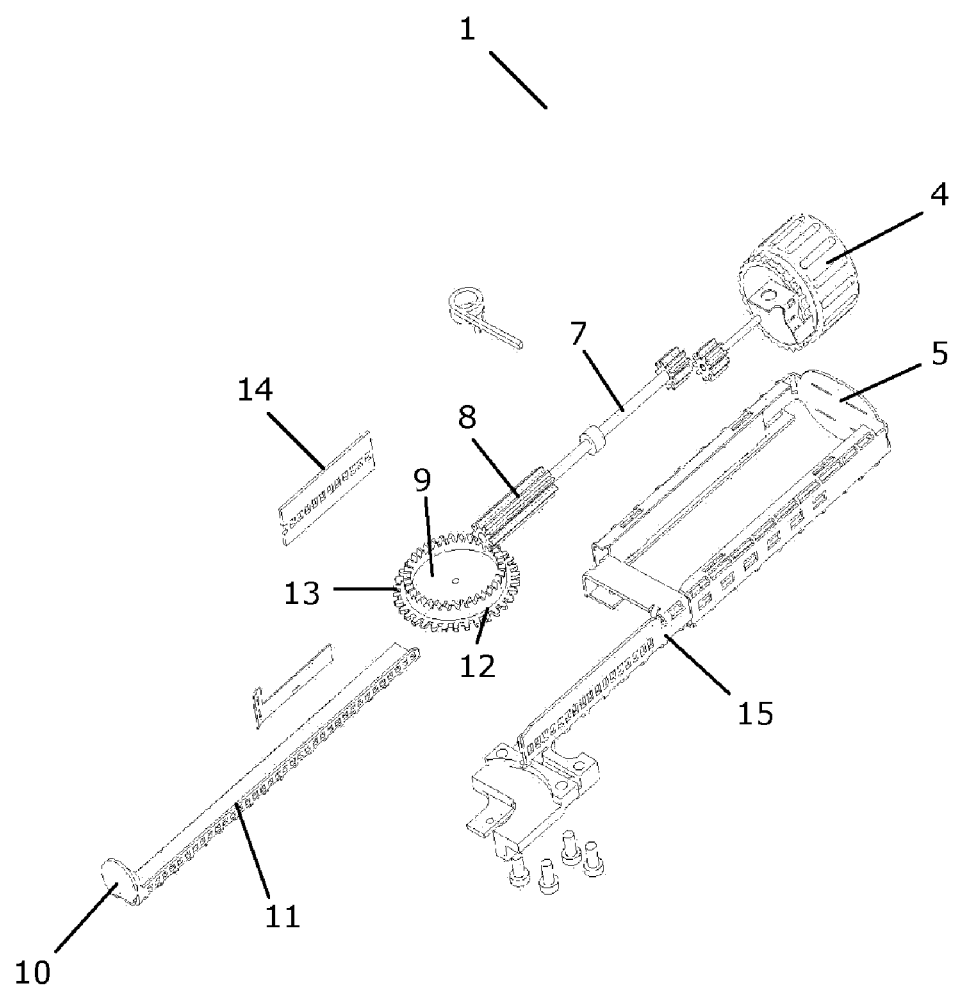

FIG. 5 is an exploded view of the injection device 1 of FIGS. 1-4. For clarity, only the parts shown in FIGS. 2-4 are shown in FIG. 5, the remaining parts having been omitted.

Since the first gear wheel 26 and the second gear wheel 12 do not rotate along with the dose setting member 4 during dose setting, the injection device 1 is compact as compared to prior art injection devices having a gearing arrangement.

Figure 6:
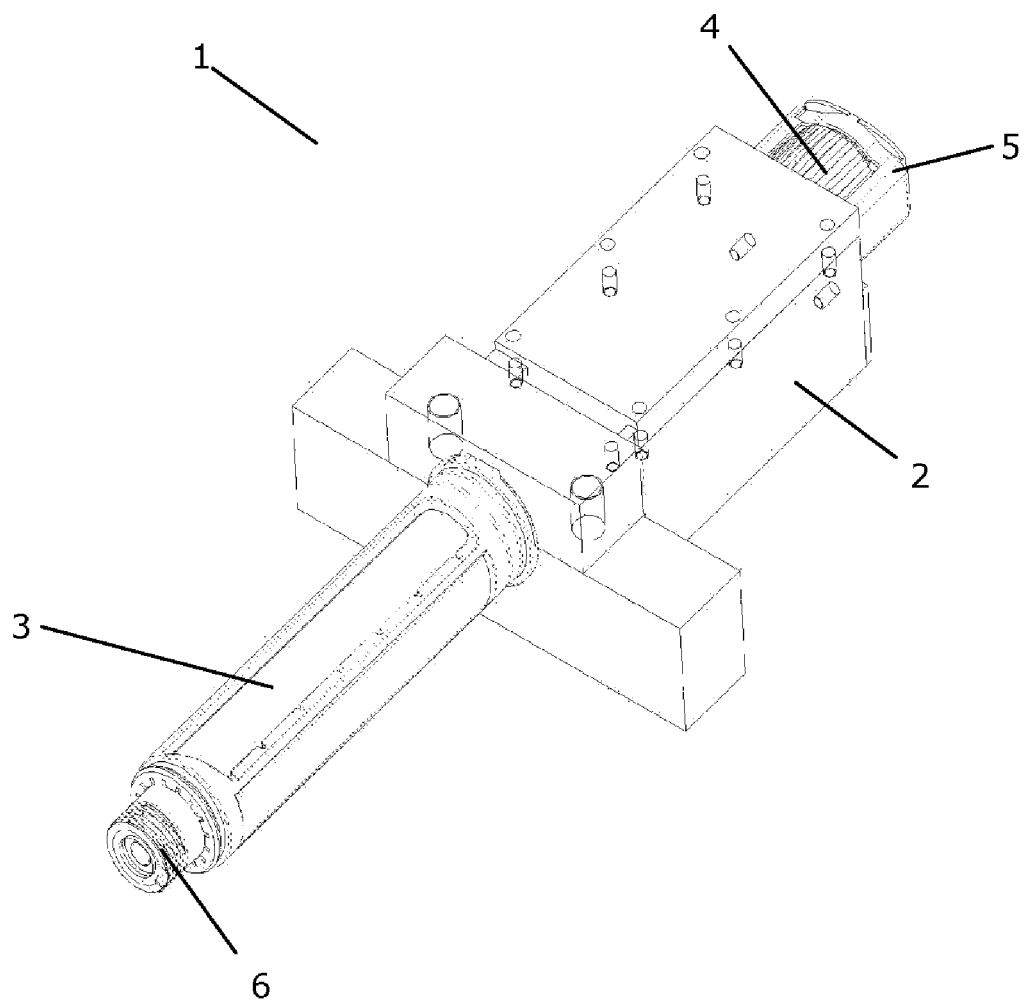
FIGS. 6-10 illustrate an injection device according to a second embodiment of the invention.

FIGS. 6-10 illustrate an injection device 1 according to a second embodiment of the invention. FIG. 6 is a perspective view of the injection device 1. The injection device 1 comprises a housing 2, a cartridge 3 containing a drug to be injected, a dose setting member 4 and an injection button 5. At a distal end 6 of the cartridge 3 it is possible to attach a needle in order to allow the drug of the cartridge 3 to be injected subcutaneously.

The operation of the injection device 1 shown in FIG. 6 will now be described with reference to FIGS. 7-10.

Figure 7:
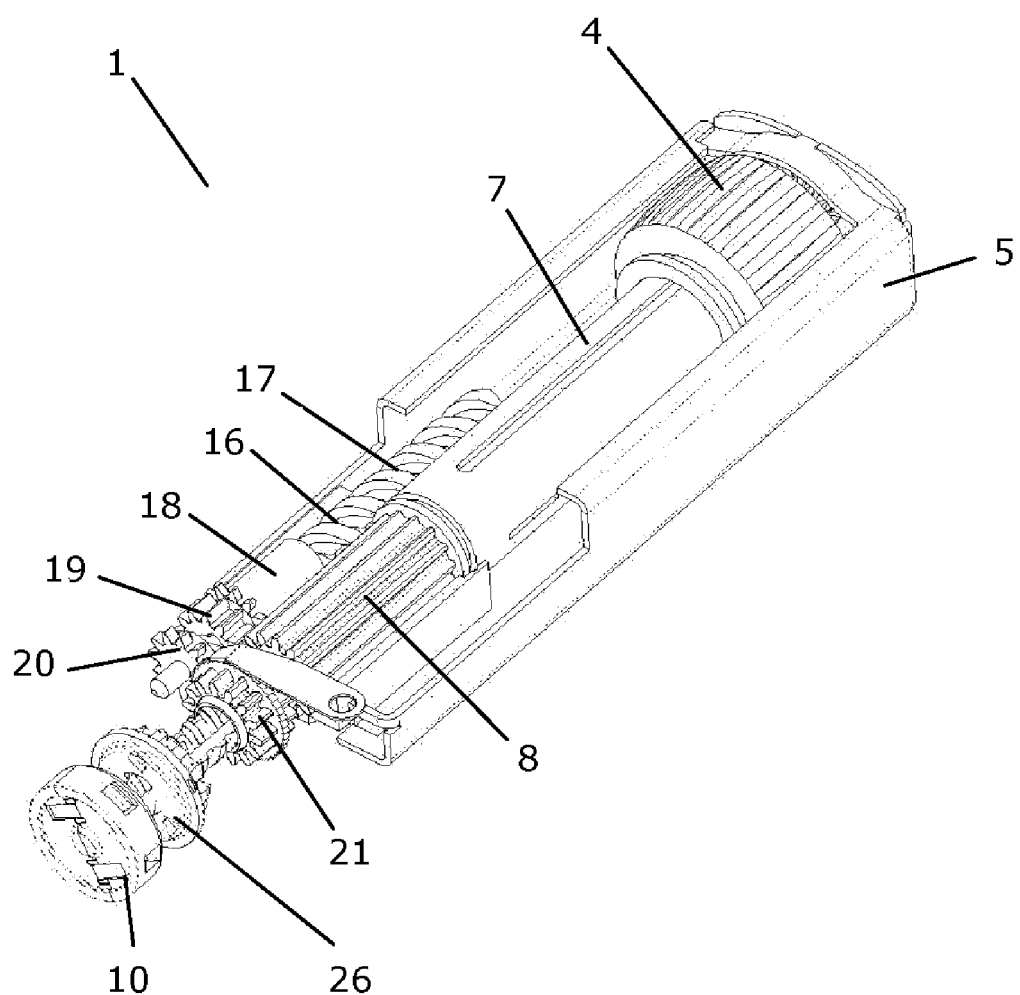

FIG. 7 shows selected parts of the injection device 1, the selected parts being essential for describing the operation of the injection device 1. Additional parts, such as the housing, which are not essential for describing the operation of the injection device 1 have been omitted for the sake of clarity.

The injection device 1 shown in FIG. 7 comprises a dose setting member 4 connected to a dose rod 7 via a key and groove connection. Arranged in parallel with the dose rod 7, and operatively connected to the dose setting member 4 via the dose rod 7, is a spindle rod 16 having an outer thread 17. A spindle nut 18 has an inner thread (not shown) which is adapted to mate with the outer thread 17 of the spindle rod 16.

The spindle nut 18 engages an extruded gear wheel 8 via a third gear wheel 19. The spindle nut 18 and the third gear wheel 19 form part of the same item, and are therefore fixed to each other. Also attached to the spindle rod 16 is a fourth gear wheel 20 which is axially locked relatively to the housing (not shown). The fourth gear wheel 20 engages a driving nut 21 coupled to a piston rod 10.

When a dose is set the dose setting member 4 is rotated, thereby rotating the dose rod 7 and the extruded gear wheel 8. Due to the engagement between the extruded gear wheel 8 and the third gear wheel 19, the spindle nut 18 is also caused to rotate. Due to the mating threads of the spindle nut 18 and the spindle rod 16, the spindle nut 18 travels axially along the spindle rod 16 in a proximal direction. The spindle nut 18 is connected to the injection button 5 via a block (not visible) in such a manner that the axial movement of the spindle nut 18 causes a corresponding axial movement of the injection button 5. The spindle nut 18 is axially locked to the injection button 5 via the block (not visible). Thus, the injection button 5 is moved away from the housing.

In FIG. 7 the injection device 1 is shown in a position in which it is ready for setting a desired dose. Thus, the injection button 5 is positioned as close as possible to the housing.

Figure 8:
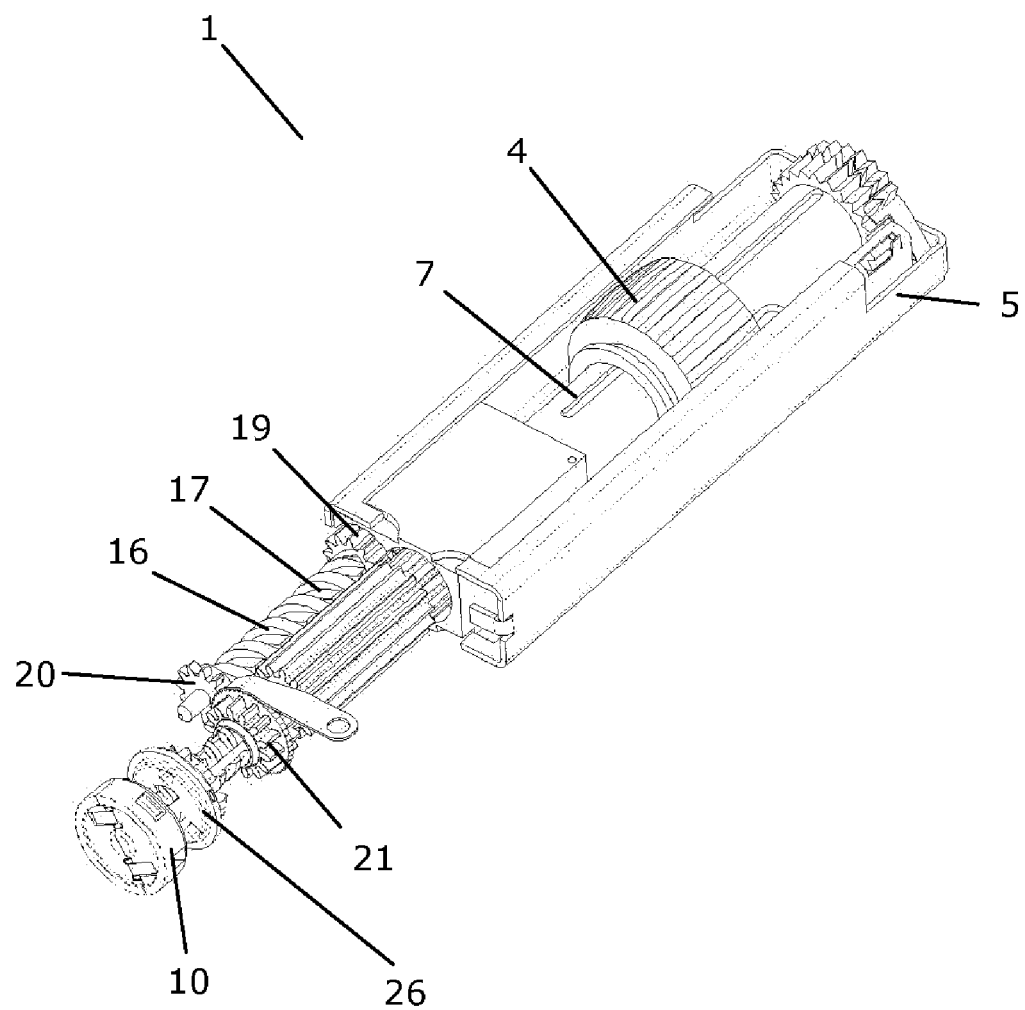

FIG. 8 shows the injection device 1 of FIGS. 6 and 7 in a position where a desired dose has been set, but not yet injected. Thus, the spindle nut (not visible) has traveled a distance along the spindle rod 16, and the injection button 5 has been moved away from the housing. When the set dose is to be injected, a user pushes the injection button 5 in a distal direction, i.e. towards the housing. Thereby the spindle nut (not visible) is also pushed in a distal direction. The spindle nut is now locked against rotation in the following manner. When the injection button 5 is pushed, a set of teeth on an item arranged in the interior of the injection button 5 are moved into engagement with a mating set of teeth arranged on the dose rod 7. This rotationally locks the dose rod 7, and thereby the extruded gear wheel 8. Since the third gear wheel 19 is engaging the extruded gear wheel 8, and since the third gear wheel 19 is connected to the spindle nut as described above, the spindle nut is thereby also rotationally locked. Accordingly, the mating threads of the spindle nut and the spindle rod 16 forces the spindle rod 16 to rotate. Due to the engagement between the fourth gear wheel 20 and the driving nut 21, the driving nut 21 is also caused to rotate. The driving nut 21 is connected to the piston rod 10 via an inner thread on the driving nut 21 and an outer thread on the piston rod 10. The piston rod 10 is locked against rotation by means of a locking member 26, and the rotation of the driving nut 21 therefore forces the piston rod 10 axially in a distal direction, thereby causing the set dose to be expelled from the cartridge. The pitch of the thread 17 on the spindle rod 16 is larger than the pitch of the thread on the piston rod 10. Thereby a gearing is provided between the axial movement of the injection button 5 and the axial movement of the piston rod 10.

Figure 9:
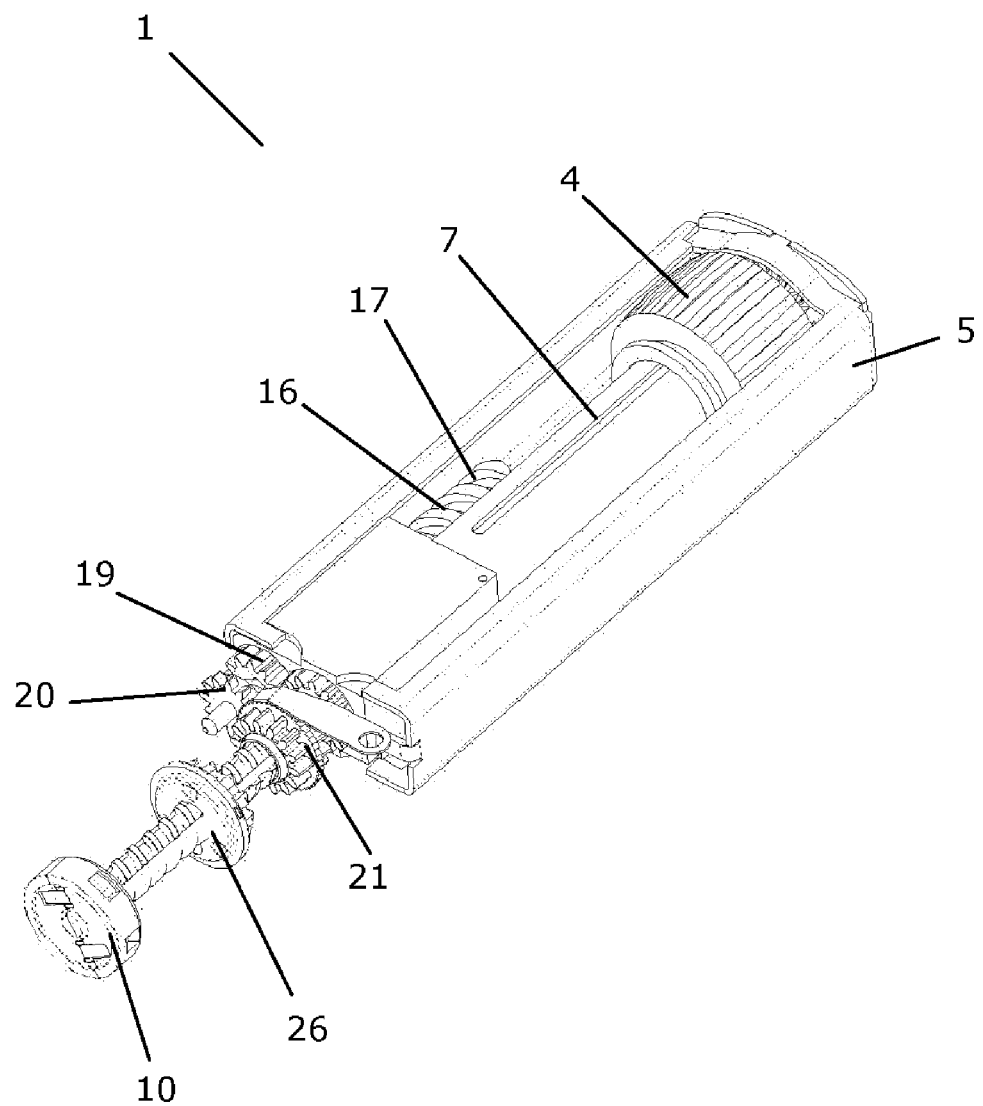

FIG. 9 shows the injection device 1 of FIGS. 6-8 in a position where a dose has just been injected. Thus, the injection button 5 and the spindle nut 18 are positioned in the same manner as in FIG. 7. However, the piston rod 10 has been moved in a distal direction, indicating that a dose has been injected.

Figure 10:
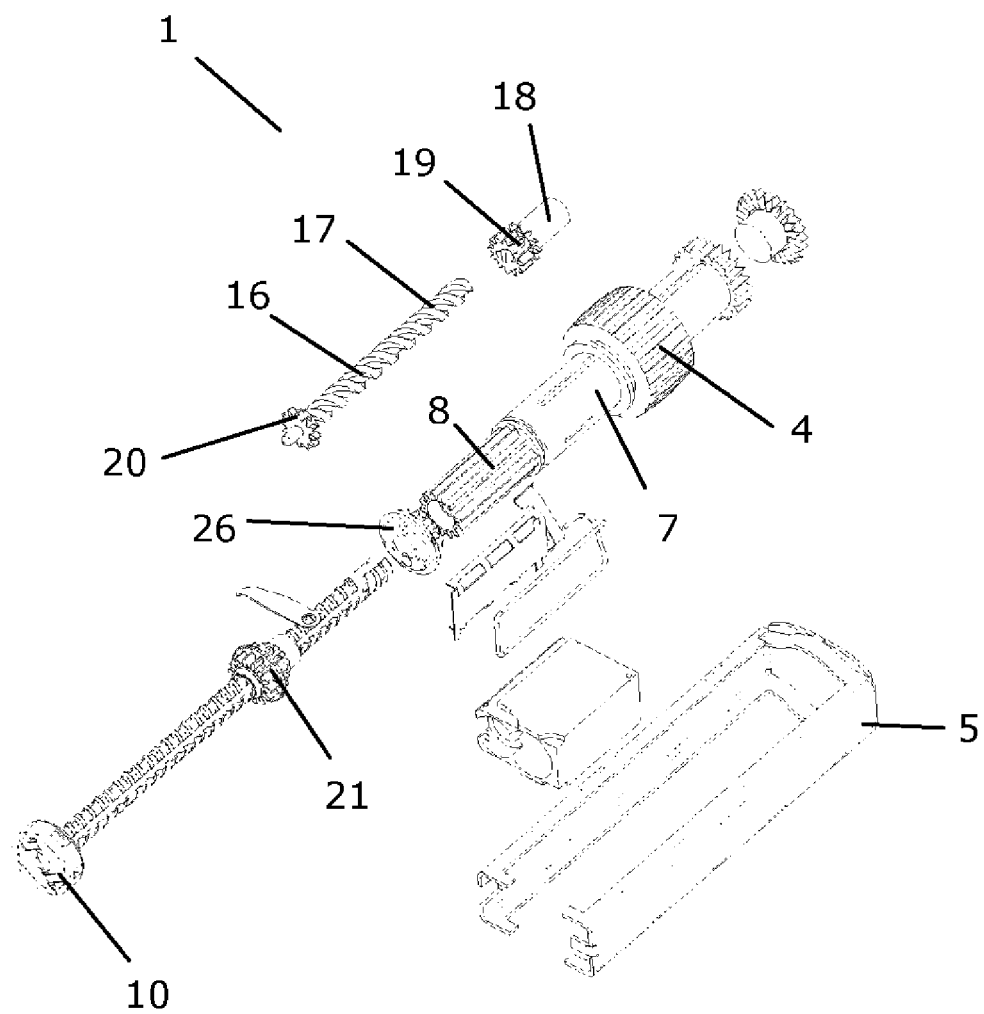

FIG. 10 is an exploded view of the injection device 1 of FIGS. 6-9. For clarity, only the parts shown in FIGS. 7-9 are shown in FIG. 10, the remaining parts having been omitted.

Since the spindle rod 16 is arranged in parallel to the dose rod 7, and since it does not rotate along with the dose setting member 4 during setting of a dose, the total size of the injection device 1 can be reduced as compared to the size of prior art injection devices having a gearing arrangement.

Figure 11:
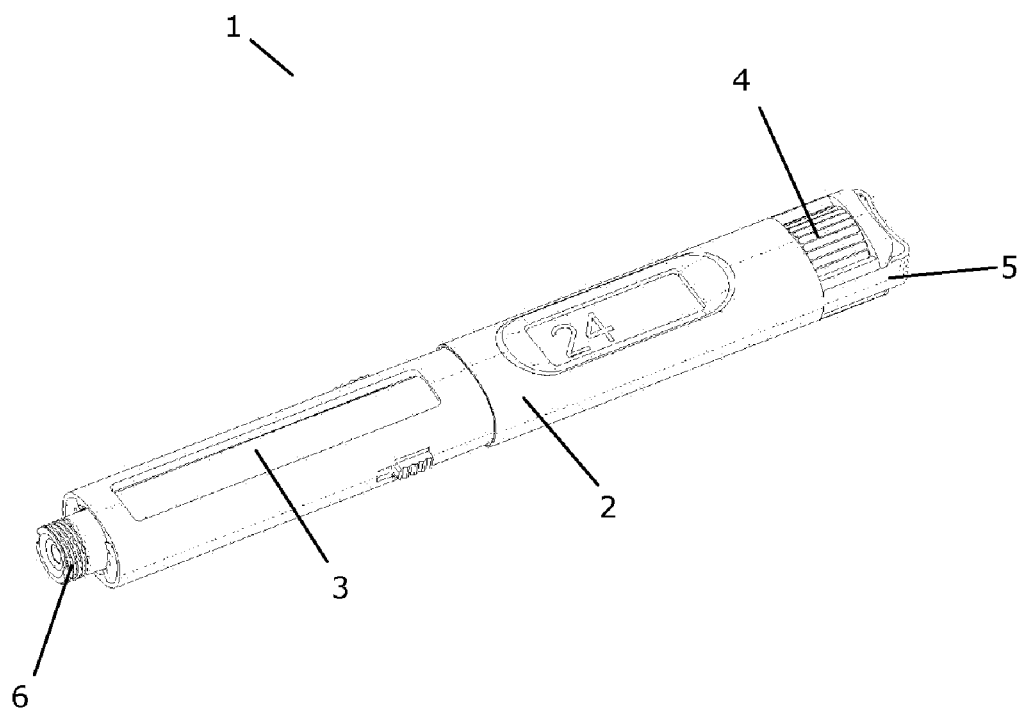
FIGS. 11-15 illustrate an injection device according to a third embodiment of the invention.

FIGS. 11-15 illustrate an injection device 1 according to a third embodiment of the invention. FIG. 11 is a perspective view of the injection device 1. The injection device 1 comprises a housing 2, a cartridge 3 containing a drug to be injected, a dose setting member 4 and an injection button 5. At a distal end 6 of the cartridge 3 it is possible to attach a needle in order to allow the drug of the cartridge 3 to be injected subcutaneously.

The operation of the injection device 1 shown in FIG. 11 will now be described with reference to FIGS. 12-15.

Figure 12:
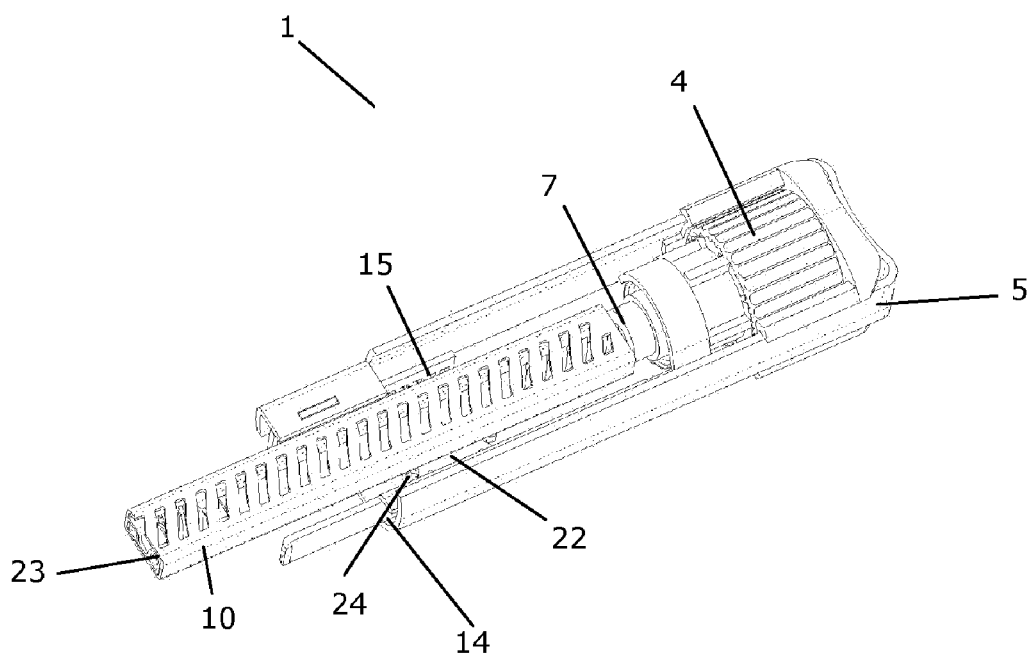

FIG. 12 shows selected parts of the injection device 1, the selected parts being essential for describing the operation of the injection device 1. Additional parts, such as the housing, which are not essential for describing the operation of the injection device 1 have been omitted for the sake of clarity.

The injection device 1 of FIG. 12 comprises a dose setting member 4 connected to a dose rod 7 via a key and groove connection. The dose rod 7 has an outer thread which mates with an inner thread of a piston rod 10. A fifth gear wheel 22 is connected to the dose rod 7 via a slide 23. The fifth gear wheel 22 is provided with a set of teeth 24 engaging a track on a first rack 14 which is substantially fixed relatively to the housing, and a track on a second rack 15 which is movable relatively to the housing and fixed relatively to the injection button 5.

When a dose is to be set, the dose setting member 4 is rotated, and thereby the dose rod 7 is also rotated. Due to the mating threads of the dose rod 7 and the piston rod 10, the dose rod 7 moves along the piston rod 10. Thereby the injection button 5 is caused to be moved in a proximal direction in the following manner. The centre of the fifth gear wheel 22 is connected to and axially locked to the dose rod 7 via slide 23. The peripheral velocity of the fifth gear wheel 22 at the point where it engages the first rack is approximately 0, and the peripheral velocity of the fifth gear wheel 22 at the point where it engages the second rack 15 is approximately twice the axial velocity of the fifth gear wheel 22. Thereby the injection button 5 is moved a distance which is approximately twice the distance traveled by the fifth gear wheel 22.

In FIG. 12 the injection device 1 is shown in a position in which it is ready for setting a desired dose. Thus, the injection button 5 is positioned as close as possible to the housing.

Figure 13:
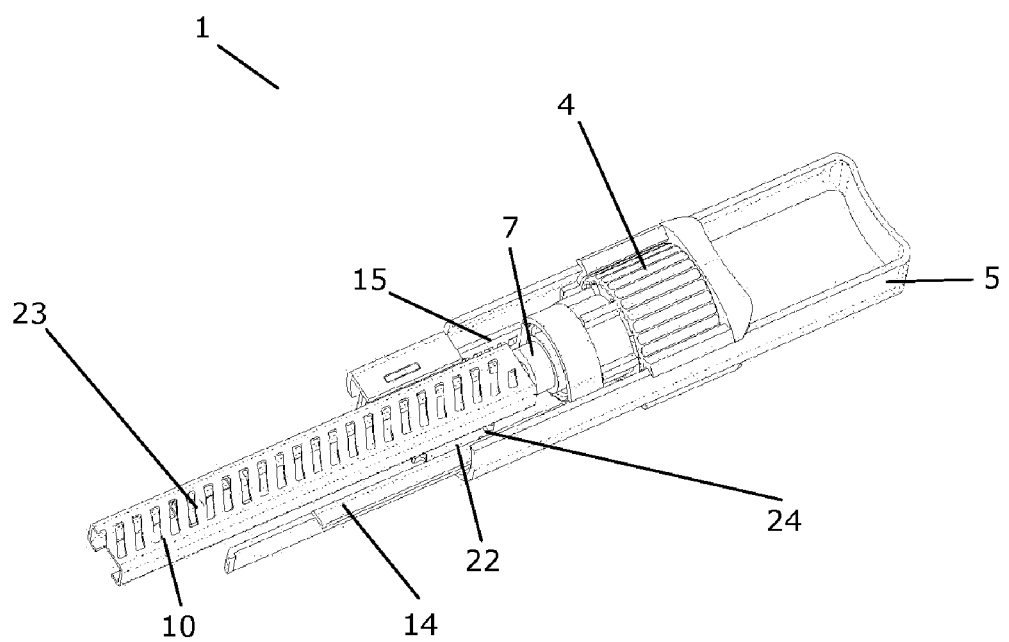

FIG. 13 shows the injection device 1 of FIGS. 11 and 12 in a position where a desired dose has been set, but not yet injected. Thus, the injection button 5 has been moved away from the housing.

When the set dose is to be injected, the user pushes the injection button 5 in a distal direction. Due to the engagement between the track on the second rack 15 and the teeth 24 of the fifth gear wheel 22, this causes the fifth gear wheel 22 to rotate and move axially. The centre of the fifth gear wheel 22 is coupled to the dose rod 7 as described above, and the dose rod 7 is prevented from rotating during injection of a set dose, because moving the injection button 5 causes the dose setting member 4 to be locked to the housing 2 due to engagement between mating teeth. The axial movement of the fifth gear wheel 22 causes the dose rod 7 to move axially. The axial movement of the dose rod 7 causes the piston rod 10 to move axially in a distal direction, thereby causing the set dose to be expelled from the cartridge.

Figure 14:
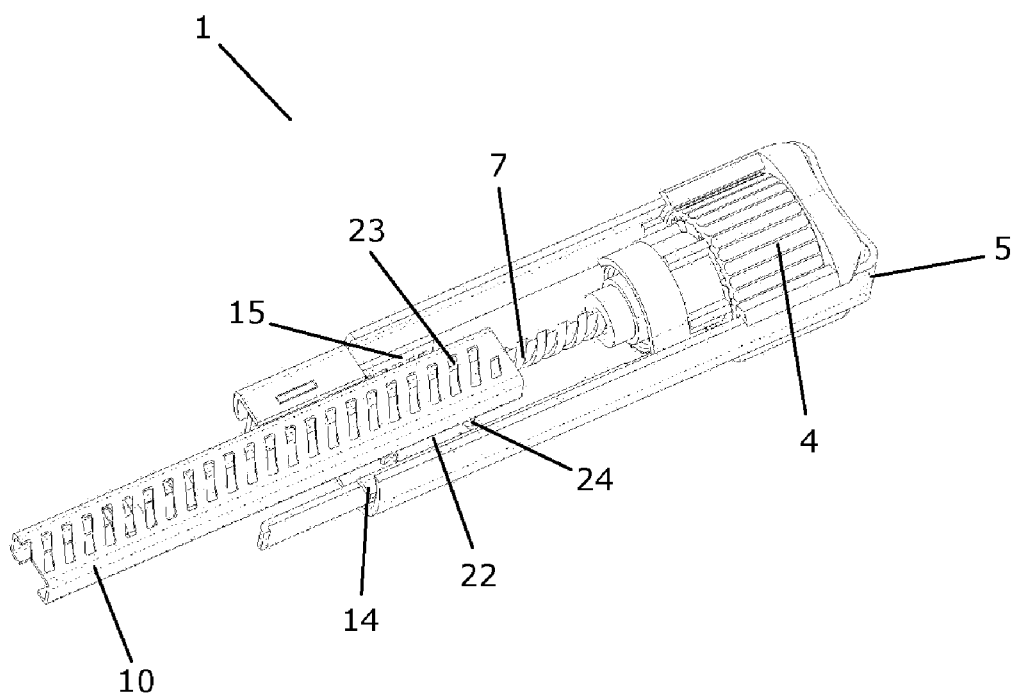

FIG. 14 shows the injection device 1 of FIGS. 11-13 in a position where a set dose has just been injected. Thus, the positions of the fifth gear wheel 22 and the injection button 5 are identical to their positions in FIG. 12. However, the piston rod 10 has been moved axially in a distal direction, indicating that a dose has been injected from the cartridge.

Figure 15:
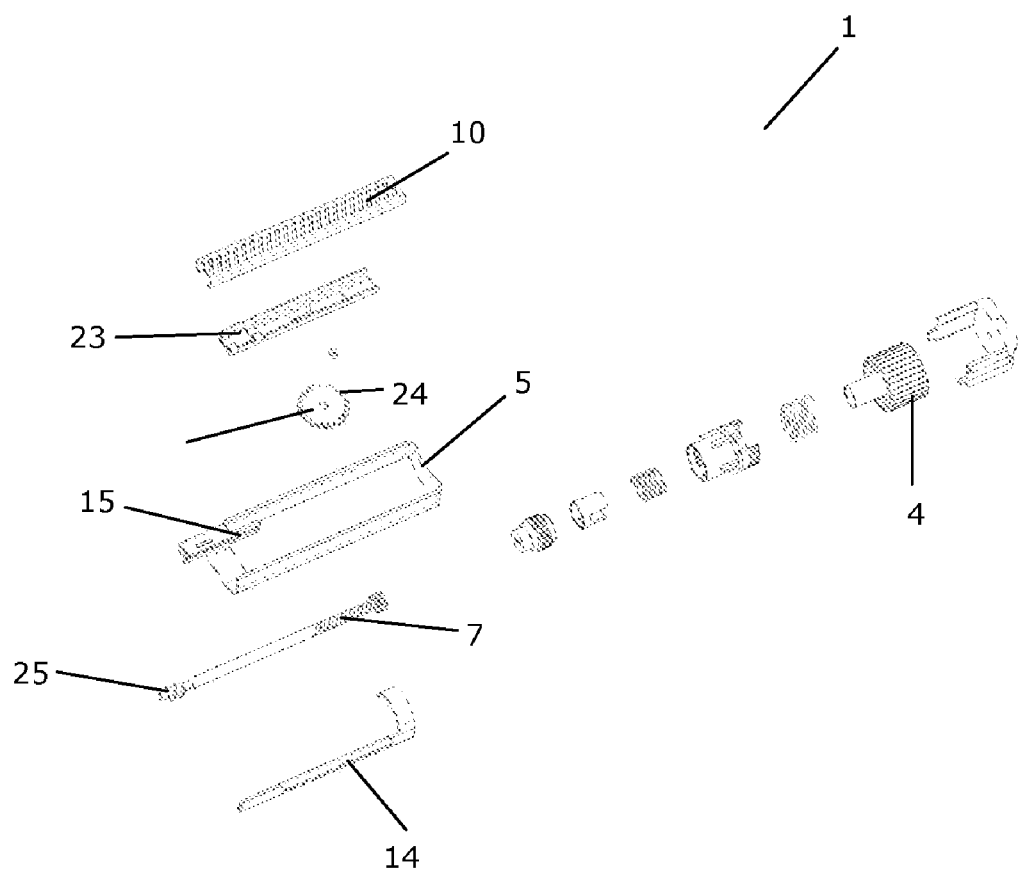

FIG. 15 is an exploded view of the injection device 1 of FIGS. 11-14. For clarity, only the parts shown in FIGS. 11-14 are shown in FIG. 15, the remaining parts having been omitted. In FIG. 15 the outer thread 25 on the dose rod 7 is visible.

Since the fifth gear wheel 22 does not rotate along with the dose setting member 4 during dose setting, it is possible to reduce the total size of the injection device 1 as compared to prior art injection devices having a gearing arrangement. The injection device 1 may, e.g., be made more flat, or additional electronics, including a display screen, a battery, etc., may be positioned in the injection device 1 without increasing the outer dimensions.

The invention claimed is:

1. An injection device comprising:
   a housing,
   a dose setting member being operable to set a dose by rotating said dose setting member relatively to the housing, about a rotational axis,
   a piston rod adapted to cause a set dose to be injected from the injection device,
   an injection button adapted to perform an axial movement, and operable to cooperate with the piston rod in injecting the set dose in such a manner that when the injection button is operated the set dose is caused to be injected by the piston rod,
   a gearing arrangement comprising at least one gear wheel, the gearing arrangement providing a gearing ratio between an axial movement of the injection button and an axial movement of the piston rod,
   wherein the gearing arrangement, during setting of a dose, is prevented from rotating along with the dose setting member about the rotational axis, and moves along the rotational axis relatively to the piston rod as the dose setting member is rotated
   wherein at least one of the gear wheel(s) has a rotational axis which is non-parallel to the rotational axis of the dose setting member, and
   during injection of the set dose, the piston rod is caused to move along with the gearing arrangement thereby maintaining its position relatively to the gearing arrangement.

2. An injection device according to claim 1, further comprising a dose rod being at least substantially rotationally locked to the dose setting member, wherein the gearing arrangement is at least substantially axially fixed to the dose rod in such a manner that the dose rod and the gearing arrangement may perform a relative rotational movement.

3. An injection device according to claim 1, wherein at least one of the gear wheel(s) has a rotational axis being at least substantially perpendicular to the rotational axis of the dose setting member.

4. An injection device according to claim 3, wherein the gearing arrangement comprises a crown wheel being operationally coupled to the dose setting member in such a manner that the crown wheel is caused to perform a rotational movement when the dose setting member is operated, said rotational movement being performed about a rotational axis which is non-parallel to the rotational axis of the dose setting member.

5. An injection device according to claim 2, wherein at least one of the gear wheel(s) has a rotational axis being at least substantially perpendicular to the rotational axis of the dose setting member.

6. An injection device according to claim 4, wherein the crown wheel is coupled to the dose setting member via an extruded gear wheel adapted to rotate along with the dose setting member about the rotational axis of the dose setting member during dose setting.

7. An injection device according to claim 4, wherein the gearing arrangement comprises a third gear wheel operationally connected to the crown wheel such that when the crown wheel is rotated, the third gear wheel is caused to move axially along the piston rod and such that when the injection button is operated to inject a set dose, the third gear wheel will move the piston rod in an axial direction.

8. An injection device according to claim 7, wherein the third gear wheel rotates coaxially with the crown wheel and wherein the third gear wheel has a set of teeth engaging a track on the piston rod.

* * * * *

UNITED STATES PATENT AND TRADEMARK OFFICE
CERTIFICATE OF CORRECTION

| | | |
|---|---|---|
| PATENT NO. | : 8,361,036 B2 | Page 1 of 1 |
| APPLICATION NO. | : 12/282446 | |
| DATED | : January 29, 2013 | |
| INVENTOR(S) | : Moller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1048 days.

Signed and Sealed this
Eighteenth Day of November, 2014

Michelle K. Lee
*Deputy Director of the United States Patent and Trademark Office*